(12) United States Patent
Nakano et al.

(10) Patent No.: US 8,691,536 B2
(45) Date of Patent: Apr. 8, 2014

(54) PECTIN LYASE, PECTIN LYASE POLYNUCLEOTIDE, ENZYME PREPARATION, AND METHOD FOR PRODUCING SINGLE CELLS OF PLANT TISSUE

(75) Inventors: Yoshihisa Nakano, Osaka (JP); Mitsuhiro Uenoyama, Osaka (JP); Erina Kobayashi, Osaka (JP)

(73) Assignees: Bio-I Co., Ltd., Osaka (JP); Nakano Yoshihisa, Osaka (JP)

( * ) Notice: Subject to any disclaimer, the term of this patent is extended or adjusted under 35 U.S.C. 154(b) by 13 days.

(21) Appl. No.: 13/502,869

(22) PCT Filed: Jul. 15, 2010

(86) PCT No.: PCT/JP2010/061981
§ 371 (c)(1),
(2), (4) Date: May 11, 2012

(87) PCT Pub. No.: WO2011/048852
PCT Pub. Date: Apr. 28, 2011

(65) Prior Publication Data
US 2012/0220016 A1 Aug. 30, 2012

(30) Foreign Application Priority Data
Oct. 19, 2009 (JP) .................. 2009-240651

(51) Int. Cl.
*C12P 19/14* (2006.01)
*C12N 9/88* (2006.01)
*C12N 15/00* (2006.01)
*C07H 21/04* (2006.01)

(52) U.S. Cl.
USPC ......... 435/99; 435/232; 435/320.1; 536/23.2; 536/23.74

(58) Field of Classification Search
None
See application file for complete search history.

(56) References Cited

FOREIGN PATENT DOCUMENTS

| JP | 03-108487 A | 5/1991 |
|---|---|---|
| WO | WO 2004/074468 A1 | 9/2004 |
| WO | WO 2009/108941 A2 | 9/2009 |

OTHER PUBLICATIONS

Ishii, S., "Enzymatic maceration of plant tissues by endo pectin lyase and endo poly galacturonase from aspergillus japonicus", Phytopathology 66:281-289, 1976.*
UniProt Accession No. A2R311, Mar. 2007, 2 pages.*
Alkorta et al., "Industrial applications of pectic enzymes: a review", Process Biochem. 33:21-28, 1998.*
International Search Report in corresponding International Application No. PCT/JP2010/061981, dated Aug. 17, 2010, 2 pages.
Harmsen, J.A.M., et al., "Cloning and expression of a second *Aspergillus niger* pectin lyase gene (pelA): Indications of a pectin lyase gene family in *A. niger*," *Curr. Genet* (1990) 18, pp. 161-166.
Kusters-van Someren, Margo A., et al., "Structure of the *Aspergillus niger pelA* gene and its expression in *Aspergillus niger* and *Aspergillus nidulans*," Curr Genet (1991) 20, pp., 293-299.
Mayans, O., et al., "Two crystal structures of pectin lyase A from *Aspergillus* reveal a pH driven conformational change and striking divergence in the substrate-binding clefts of pectin and pectate lyases," *Structure*, 1997, vol. 5, No. 5, pp. 677-689.
Nozaki, Kazuhiko, "Antimicrobial Activity of Pectin Lysates and Their Application," *The Society for Antibacterial and Antifungal Agents*, Japan Nenji Taikai Yoshishu, 2001, pp. 96-97.
Nozaki, Kazuhiko, "Chemical preservation techniques of foods; Chapter Two: Existing Preservative; An Extract from Milt Protein (Protamine) and a Product of the Decomposition of Pectin," *Journal of Antibacterial and Antifungal Agents*, 37(10), Oct. 10, 2009, pp. 773-781.
Pel, Herman J., et al., "Genome sequencing and analysis of the versatile cell factory *Aspergillus niger* CBS 513.88," Nature Biotechnology, 2007, 25(2), pp. 221-231.
Yokotsuka, Koki, et al., "Antibacterial activity of pectin hydrolysates," *Hakkokogaku Kaishi*, 1984, 62(1), pp. 1-7.

* cited by examiner

*Primary Examiner* — David J Steadman
(74) *Attorney, Agent, or Firm* — Brinks Gilson & Lione

(57) ABSTRACT

To provide a pectin lyase and a gene for a pectin lyase which can be used in an enzyme preparation for processing plant tissue, and which possesses sufficient maceration activity even under highly acidic conditions. Isolation and purification of a pectin lyase and a gene for a pectin lyase having a molecular weight of 39,500 produced by an *Aspergillus* filamentous fungus, and possessing a maceration activity and a pectin lyase activity. The pectin lyase has a specified amino acid sequence, an optimal pH of 3.5 for maceration activity, an optimal pH of 4.5 for pectin lyase activity, and deactivates with boiling treatment for 15 minutes at 121° C. Sterilizing heat treatment are unnecessary, because the present invention possesses sufficient maceration activity at pH 3.0-4.0, and the resulting pectin lysate possesses a bactericidal activity and a potent antibacterial activity. It is possible to inexpensively mass produce food products which retain water-soluble components within the cell, because physical treatment such as stirring or beating is also unnecessary.

9 Claims, 4 Drawing Sheets

SEQUENCE LISTING

<160> NUMBER OF SEQ ID NOS: 9

<210> SEQ ID NO 1
<211> LENGTH: 8
<212> TYPE: PRT
<213> ORGANISM: Aspergillus sp.

<400> SEQUENCE: 1

Val Gly Val Ser Gly Ser Ala Glu
1               5

<210> SEQ ID NO 2
<211> LENGTH: 359
<212> TYPE: PRT
<213> ORGANISM: Aspergillus sp.

<400> SEQUENCE: 2

Val Gly Val Ser Gly Ser Ala Glu Gly Phe Ala Glu Gly Val Thr Gly
1               5                   10                  15

Gly Gly Ser Ala Thr Pro Val Tyr Pro Asp Thr Ile Asp Glu Leu Val
            20                  25                  30

Ser Tyr Leu Gly Asp Asp Glu Ala Arg Val Ile Val Leu Thr Lys Thr
        35                  40                  45

Phe Asp Phe Thr Asp Ser Glu Gly Thr Thr Gly Thr Gly Cys Ala
    50                  55                  60

Pro Trp Gly Thr Ala Ser Ala Cys Gln Val Ala Ile Asp Gln Asp
65                  70                  75                  80

Trp Cys Glu Asn Tyr Glu Pro Asp Ala Pro Ser Val Ser Val Glu Tyr
                85                  90                  95

Tyr Asn Ala Gly Thr Leu Gly Ile Thr Val Thr Ser Asn Lys Ser Leu
                100                 105                 110

Ile Gly Glu Gly Ser Ser Gly Ala Ile Lys Gly Lys Gly Leu Arg Ile
            115                 120                 125

Val Ser Gly Ala Glu Asn Ile Ile Ile Gln Asn Ile Ala Val Thr Asp
        130                 135                 140

Ile Asn Ala Lys Tyr Val Trp Gly Gly Asp Ala Ile Thr Leu Asp Asp
145                 150                 155                 160

Cys Asp Leu Val Trp Ile Asp His Val Thr Thr Ala Arg Ile Gly Arg
                165                 170                 175

Gln His Tyr Val Leu Gly Thr Ser Ala Asp Asn Arg Val Ser Leu Thr
            180                 185                 190

Asn Asn Tyr Ile Asp Gly Val Ser Asp Tyr Ser Ala Thr Cys Asp Gly
        195                 200                 205

Tyr His Tyr Trp Ala Ile Tyr Leu Asp Gly Asp Ala Asp Leu Val Thr
    210                 215                 220

Met Lys Gly Asn Tyr Ile Tyr His Thr Ser Gly Arg Ser Pro Lys Val
225                 230                 235                 240

Gln Asp Asn Thr Leu Leu His Ala Val Asn Asn Tyr Trp Tyr Asp Ile
                245                 250                 255

Ser Gly His Ala Phe Glu Ile Gly Glu Gly Gly Tyr Val Leu Ala Glu
            260                 265                 270

Gly Asn Val Phe Gln Asn Val Asp Thr Val Leu Glu Thr Tyr Glu Gly
        275                 280                 285

Glu Ala Phe Thr Val Pro Ser Thr Thr Ala Gly Glu Val Cys Ser Thr
    290                 295                 300

```
Tyr Leu Gly Arg Asp Cys Val Ile Asn Gly Phe Gly Ser Ser Gly Thr
305                 310                 315                 320

Phe Ser Glu Asp Ser Thr Ser Phe Leu Ser Asp Phe Glu Gly Lys Asn
                325                 330                 335

Ile Ala Ser Ala Ser Ala Tyr Thr Ser Val Ala Ser Ser Val Val Ala
            340                 345                 350

Asn Ala Gly Gln Gly Asn Leu
        355

<210> SEQ ID NO 3
<211> LENGTH: 1289
<212> TYPE: DNA
<213> ORGANISM: Aspergillus sp.

<400> SEQUENCE: 3
gtcggcgtgt ccggctctgc tgagggtttc gccgagggcg ttaccggtgg tggcagtgcc      60
accccgtct accccgatac tatcgatgag ctggtctcct acctcggaga cgatgaggcc     120
cgcgtcattg tcctgaccaa gaccttcgac ttcaccgaca gcgaaggtac taccactggc     180
actggttgcg ctccctgggg taccgcctcc gcttgccagg ttgctattga ccaggacgac     240
tggtgcgaga actacgagcc cgatgctccc tctgtcagcg ttgaatagta tgtccttgcc     300
ggctgtcatc cgcttttgat ctcgtatcta accttgaata gctacaacgc tggtaccctc     360
ggtatcaccg tcacctccaa caagtccctc atcggtgagg ctcctctgg tgccattaag      420
ggcaagggtc tccgcattgt cagcggtgct gagaacatca tcatccagta ggttatactc     480
agtgtcattt ggaaattact ctaacaaaat caggaacatc gccgttaccg acatcaacgc     540
caagtacgtc tggggtggtg atgctattac tcttgatgac tgcgacctgg tctggatcga     600
ccacgttact gtaagccttc acttcttcac ttttactaaa tcaagagcgt caagttaaca     660
aatgacagac cgcccgcatt ggtcgccagc actacgtcct cggaaccagc gccgacaacc     720
gcgtctctct caccaacaac tacattgacg gtgtctccga ctactccgcc acctgcgatg     780
gctaccacta ctgggccatc taccttgacg gtgacgccga cttggtcacc atgaagggca     840
actacatcta ccacacctcc ggccgttccc ccaaggtcca ggacaacact ctcctccacg     900
ctgtaagttc tatctctgcc ggtcaccttc gactcaacta accaccaaca taggtcaaca     960
actactggta cgacatctcc ggccacgcct tcgagatcgg tgagggtggc tacgtcttgg    1020
ctgagggtaa cgtttttccag aacgttgaca ctgttcttga gacctatgag ggcgaggcct    1080
tcaccgtccc ctccaccacc gccggtgaag tctgctccac ctaccttggc cgtgactgtg    1140
tcatcaacgg cttcggctcc tccggcactt tctccgagga cagcacctct ttcctctccg    1200
acttcgaggg caagaacatt gcctctgctt cggcttacac ctctgttgcc tctagcgttg    1260
ttgccaacgc cggtcagggc aacctgtaa                                      1289

<210> SEQ ID NO 4
<211> LENGTH: 1080
<212> TYPE: DNA
<213> ORGANISM: Aspergillus sp.

<400> SEQUENCE: 4
gtcggcgtgt ccggctctgc tgagggtttc gccgagggcg ttaccggtgg tggcagtgcc      60
accccgtct accccgatac tatcgatgag ctggtctcct acctcggaga cgatgaggcc     120
cgcgtcattg tcctgaccaa gaccttcgac ttcaccgaca gcgaaggtac taccactggc     180
actggttgcg ctccctgggg taccgcctcc gcttgccagg ttgctattga ccaggacgac     240
```

```
tggtgcgaga actacgagcc cgatgctccc tctgtcagcg ttgaatacta caacgctggt      300 acccctcggta tcaccgtcac ctccaacaag tccctcatcg gtgagggctc ctctggtgcc     360
attaagggca agggtctccg cattgtcagc ggtgctgaga acatcatcat ccagaacatc      420
gccgttaccg acatcaacgc caagtacgtc tggggtggtg atgctattac tcttgatgac      480
tgcgacctgg tctggatcga ccacgttact accgcccgca ttggtcgcca gcactacgtc      540
ctcggaacca gcgccgacaa ccgcgtctct ctcaccaaca actacattga cggtgtctcc      600
gactactccg ccacctgcga tggctaccac tactgggcca tctaccttga cggtgacgcc      660
gacttggtca ccatgaaggg caactacatc taccacacct ccggccgttc ccccaaggtc      720
caggacaaca ctctcctcca cgctgtcaac aactactggt acgacatctc cggccacgcc      780
ttcgagatcg gtgagggtgg ctacgtcttg gctgagggta acgttttcca gaacgttgac      840
actgttcttg agacctatga gggcgaggcc ttcaccgtcc cctccaccac cgccggtgaa      900
gtctgctcca cctaccttgg ccgtgactgt gtcatcaacg gcttcggctc ctccggcact      960
ttctccgagg acagcacctc tttcctctcc gacttcgagg gcaagaacat tgcctctgct     1020
tcggcttaca cctctgttgc ctctagcgtt gttgccaacg ccggtcaggg caacctgtaa     1080
```

<210> SEQ ID NO 5
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is i
<220> FEATURE:
<221> NAME/KEY: misc_feature
<222> LOCATION: (6)..(6)
<223> OTHER INFORMATION: n is i
<220> FEATURE:
<221> NAME/KEY: misc_feature
<222> LOCATION: (9)..(9)
<223> OTHER INFORMATION: n is i
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 5

```
gtnggngtnw snggnwsngc                                                   20
```

<210> SEQ ID NO 6
<211> LENGTH: 11
<212> TYPE: DNA
<213> ORGANISM: Aspergillus sp.

<400> SEQUENCE: 6

```
tccggctctg c                                                            11
```

<210> SEQ ID NO 7
<211> LENGTH: 20
<212> TYPE: DNA
<213> ORGANISM: Artificial Sequence
<220> FEATURE:

-continued

```
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 7
gtnggngtnt ccggctctgc                                          20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ccccgtctac cccgatacta                                          20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
caacaacgct agaggcaaca                                          20
```

PECTIN LYASE, PECTIN LYASE POLYNUCLEOTIDE, ENZYME PREPARATION, AND METHOD FOR PRODUCING SINGLE CELLS OF PLANT TISSUE

This application is a National Stage of International Application PCT/JP2010/061981, filed Jul. 15, 2010, which claims the benefit of the filing date of Japanese Patent Application No. 2009-240651, filed Oct. 19, 2009. The entirety of both applications is hereby incorporated by reference.

TECHNICAL FIELD

The present invention relates to a pectin lyase possessing maceration activity, as well as a pectin lyase gene, an enzyme preparation containing the pectin lyase, and a method for producing single cells of plant tissue using the pectin lyase.

BACKGROUND ART

Pectin is a complex polysaccharide which is present primarily in the intercellular layers of plants, and which functions as an adhesive substance among cells. Pectin-degrading enzymes are generally referred to as pectinases.

Pectinases are used not only in food processing such as refining of fruit juices, but they are also used in fields such as the refining of fibers (e.g., Patent Reference 1), and in addition, attempts have been made to use them in pharmaceuticals (e.g., Patent Reference 2). With this diversification in demand, novel pectinases have been sought which have a variety of optimal pH and temperature characteristics, depending on the purpose for their use.

Patent Reference 1: Japanese Patent Application Kokai Publication No. 2009-35853

Patent Reference 2: Japanese Patent Application Kokai Publication No. H09-315999

Among the pectinases, some types of enzymes break down plant fibers by reducing the molecular weight, fragmenting, or dissolving insoluble pectin (protopectin) present in the intercellular layers of plants, and also exhibit activity which frees single cells from each other (known as maceration or protopectinase activity, but referred to in this Specification as "maceration activity"). On the other hand, there are also enzymes which possess pectin-degrading activity but which do not possess maceration activity, and even if they exhibit both types of activity, the enzymes may have a different optimal pH for each respective activity.

Enzymes possessing maceration activity are necessary, along with cellulase, for isolating protoplasts from plants and indispensible for fundamental botanical research. It has been reported that enzymes such as polygalacturonase and polymethylgalacturonase which hydrolyze the α-1,4 bond of polygalacturonic acid, and lyases such as pectin lyase and pectate lyase which cleave these bonds with a β-elimination reaction, also possess some type of maceration activity.

Soft plant rot is known to occur as a softening plant disease in which plant tissues are degraded by these maceration enzymes which are produced by microorganisms. Among these, pectate lyase, derived from the genus *Erwinia*, is well known (Florence Tardy, William Nasser, Janine Robert-Baudouy, and Nicole Hugouvieux-Cotte-Pattat, *J. Bacteriol.,* 179, 2503-2511, April 1997).

Detailed research has been conducted regarding *Erwinia*-derived pectate lyases and on the relationship between their maceration activity and pectinase activity. For example, Pectate lyase C (PelC), derived from *Erwinia chrysanthemi*, is a pectinase which has pectate lyase activity and maceration activity. Comparing experiments on single or double amino acid changes of PelC in various PelC produced using a method of site-specific elicitation of mutations described later have shown that these enzymes possess their respective intrinsic pectate lyase activity and maceration activity which is proportional to the pectate lyase activity (Nobuhiro Kita, Carol M. Boyd, Michael R. Garrett, Frances Jurnak, and Noel T. Keen, *J. Biol. Chem.,* 271, 26529-26535, Oct. 25, 1996). It should be noted that all of the pectate lyases appearing in the article had an optimal pH on the alkaline side, regardless of the microorganism from which they were derived.

Maceration enzyme preparations for the industrial use are primarily derived from microorganisms such as filamentous fungi belonging to the genus *Aspergillus* and *Rhizopus*, and microorganisms in the genus *Bacillus*. For example, Pectolyase Y-23 (Registered trademark of Kyowa Hakko Co., Ltd.) is an enzyme preparation used in research which contains, as primary enzymes, pectin lyases and polygalacturonases derived from *Aspergillus japonicum*, and is well known for its potent maceration activity. The optimal pH of Pectolyase Y-23 is 5.5. Macerozyme R10 (Registered trademark of Yakult Pharmaceutical Co.) is also widely used. Macerozyme R10 is a pectinase preparation which has polygalacturonase activity and an optimal pH of 5.0. In these fields of basic research, there is a desire for novel maceration enzymes with optimal pH values which are tailored to the characteristics of plants.

These maceration enzymes are used not only in basic research on plants, but efforts have also been made to use them in the manufacture of food products by single cell formation of plants (e.g., Patent Reference 3). In comparison with extraction using alcohols and hot-water extraction in manufacturing processes for botanical functional raw materials, single cell formation of plants using maceration enzymes is a milder process which is implemented at normal temperatures and pressures. It therefore does little harm to the environment, and has the advantages that the natural plant components are not readily modified and the taste of the resulting food is enhanced, because of a masking effect on intracellular components by the cell wall and the cell membrane.

Patent Reference 3: Japanese Patent Application Kokai Publication No. H09-75026

In the conventional mass production of food products by single cell formation of plants using maceration enzymes, there was the problem of low yields from plant raw materials, because large quantities of undissociated tissue remained after enzymatic reactions. It was thus necessary to carry out prolonged enzymatic treatment or to use physical treatment such as stirring or beating, in order to raise yields.

However, when prolonged enzymatic treatment was carried out for 1-2 days under mild conditions such as normal temperature, for example, harmful microorganisms remaining in the raw materials grew during the enzymatic reaction, and it was difficult to separate the plant cell product from the harmful microorganisms with a filter, so it was necessary to sterilize by heating the enzymatic reaction solution to about 100° C. If enzymatic treatment is carried out at about 40° C. over a short period of 3-5 hours, some degree of vigorous stirring or beating was needed (for example, in Patent Reference 4, in which is described a mechanism provided with a spiral stirring member held rotatable around an axis of rotation in a tube forming an enzymatic treatment unit). These treatments significantly destroy or damage cell membranes formed from lipid double membranes, making it difficult to retain the natural components, in particular the water-soluble components, within the cell.

Patent Reference 4: Japanese Patent No. 3,986,541

In view of the current state and problems of the prior art, the present invention has as its object to provide a novel pectin lyase, a pectin lyase gene, an enzyme preparation containing the pectin lyase, and a method for producing single cells of plant tissue, which is capable of improving yields from plant raw materials when obtaining single cells from plant tissue by using a maceration enzyme, and when producing food by single cell formation of plants, without needing heat treatment for sterilization which was necessary when carrying out prolonged enzymatic treatment, or physical treatment such as stirring or beating.

DISCLOSURE OF THE INVENTION

Problems to be Solved by the Invention

In order to solve the above problems, the present inventors believed that if they were able to produce a pectinase having a potent maceration activity, they could enhance the yields from plant raw materials while reducing the enzymatic reaction time and reducing the growth of microorganisms. On the other hand, the present inventors noted the fact that at a pH of 5.0 or lower, pectin hydrolysates possess distinct antibacterial activity with respect to E. coli, P. aeruginosa, S. aureus, and B. subtilis (as reported, for example, by Koki Yokotsuka, Toshihide Matsudo, Tadae Kushida, Shigeo Inamine, and Tomoyoshi Nakajima in Hakkogaku Kaishi, 62, 1-7, Jan. 25, 1984). Accordingly, the present inventors studied pectin hydrolysates under conditions which inhibit microbial growth, and discovered that a synergetic effect with regard to antibacterial activity occurs if pectin hydrolysates are used in combination with highly acidic conditions with pH in the vicinity of 3.0, an environment in which microbial growth is difficult.

Accordingly, first, there was found to be an inhibiting effect on microbial growth when the formation of single cells was attempted using a variety of commercially available maceration enzymes under conditions of pH 3.0, but this approach was not sufficiently practical, because the cell count generally exceeded 3,000/g. It was therefore necessary to study maceration enzymes which effectively produce pectin hydrolysates which possess a stronger antibacterial activity.

Maceration enzymes which readily act on high methyl ester pectin are effective, because pectin hydrolysates exhibit stronger antibacterial activity when the methylesterification of their carboxyl groups is higher. Accordingly, the present inventors believed that if it were possible to produce a novel enzyme which possesses a potent maceration activity in the vicinity of pH 3.0 and which forms pectin hydrolysates with a high degree of methylesterification, then it would be possible to prevent the growth of harmful microorganisms by means of the antibacterial activity of the pectin hydrolysates, even under mild enzymatic reaction conditions of normal temperatures, and also possible to inexpensively produce food products, because no heat sterilization is needed in single cell formation of plants, which does not destroy or damage cellular attributes, in particular cell membranes.

The problem to be solved by the present invention is that in the prior art, there were no maceration enzymes which were sufficiently active under highly acidic conditions in the vicinity of pH 3.0 and which yielded pectin hydrolysates with strong antibacterial activity when food products were produced by single cell formation of plants by using maceration enzymes.

Such maceration enzymes are useful when obtaining fresh single cells from plant tissues of various plant species which grow under highly acidic conditions. The present invention further provides a gene which codes for a maceration enzyme, as well as an enzyme preparation, and a method for producing single cells of plant tissue, such that the maceration enzyme is useful in applications of a greater scale.

Means for Solving the Problems of the Prior Art

To solve the above problems of the prior art, the present invention provides a protein, enzyme preparation, gene, and method for producing single cells of plant tissue, which are described as follows.

[1] A protein having the characteristics a)-g) below.
 a) Produced by an *Aspergillus* filamentous fungus
 b) Possesses maceration activity and pectin lyase activity
 c) Molecular weight of 39,500
 d) Optimal pH of 3.5 for maceration activity
 e) Optimal pH of 4.5 for pectin lyase activity
 f) Deactivates with boiling treatment for 15 minutes at 121° C., and
 g) Has the N-terminus formed from the amino acid sequence given in SEQ ID NO: 1.

[2] Protein (a) or (b) below.
 (a) A protein having the amino acid sequence given in SEQ ID NO: 2
 (b) A protein having an amino acid sequence in which 1 or a plurality of amino acids in the amino acid sequence given in SEQ ID NO: 2 is (are) deleted, substituted, or added, and also having a maceration activity.

[3] An enzyme preparation containing a protein according to [1] or [2] above, and used for processing plant tissues or plant tissue-derived substances by degrading pectin.

[4] An enzyme preparation wherein the enzyme preparation according to [3] above is also caused to contain any one or more components of cellulase, xylanase, protease, galactanase, arabinanase, mannanase, rhamnogalacturonase, pectin methylesterase, pectate lyase, and other pectin lyases and polygalacturonases.

[5] A method for producing single cells of plant tissue using an enzyme preparation according to [3] or [4] above as a maceration enzyme, comprising causing the maceration enzyme to act on the plant tissue under acidic conditions of pH 3.0-3.5, and preventing the growth of harmful microorganisms by means of the antibacterial activity of a pectin lysate, without needing a sterilizing heat treatment.

[6] A gene coding for a protein of (a) or (b) below.
 (a) A protein having the amino acid sequence given in SEQ ID NO: 2
 (b) A protein having an amino acid sequence in which 1 or a plurality of amino acids in the amino acid sequence given in SEQ ID NO: 2 is (are) deleted, substituted, or added, and also having a maceration activity.

[7] A gene formed from a DNA of (a) or (b) below.
 (a) A DNA formed from the base sequence given in SEQ ID NO: 4.
 (b) A DNA coding for a protein hybridized under stringent conditions from DNA formed entirely from the base sequence given in SEQ ID NO: 4 or from DNA formed partly from complementary base sequence, and also having a maceration activity.

[8] A gene consisting of DNA formed from the base sequence given in SEQ ID NO: 3.

Advantageous Effects of the Invention

According to the present invention, it is possible to prevent the growth of harmful microorganisms by means of the antibacterial activity of a pectin lysate, even under mild enzymatic reaction conditions of normal temperatures, because a pectin lyase is produced which has a potent maceration activity even under highly acidic conditions in the vicinity of pH 3.0, in which the maceration activity has an optimal pH of 3.5, and the resulting pectin lysate has a strong antibacterial activity. Therefore, if the present invention is employed, heat treatment for sterilization is no longer needed, and physical treatment such as stirring and beating are also no longer needed, therefore making it possible to prevent destroying or damaging the cell membranes, and making it possible to inexpensively mass produce food products which retain the water-soluble components within the cell.

Furthermore, if the present invention is used to form single cells of plant tissues of species which grow under highly acidic conditions, it is possible to obtain fresh single cells in high yield, because microbial contamination is reduced, since there is little damage to plant cells because the pH is suitable for the plants. As long as fresh single cells are harvested in high yield, they are also useful in performing various subsequent experiments, such as plant cell culturing.

DETAILED DESCRIPTION OF THE PREFERRED EMBODIMENTS

Figure 1:
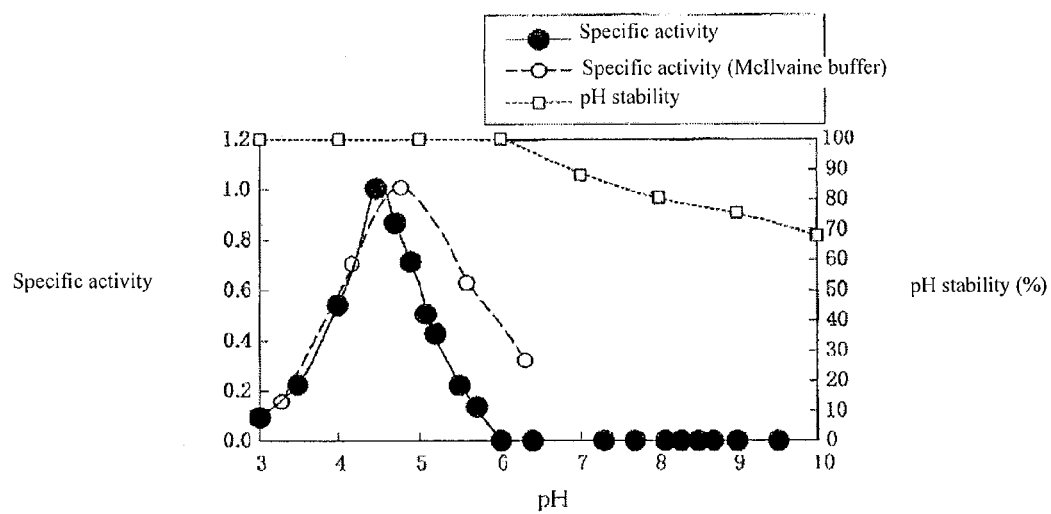
FIG. 1 is a graph showing experimental results confirming the optimal pH and the pH stability of the pectin lyase of the present invention. The specific activity is given in terms of an activity of 1.0 at pH of 4.5 (acetate buffer) or pH 4.8 (McIlvaine buffer), and the pH stability is evaluated by computing as follows: (Activity after settling)/(Activity before settling)× 100.

As a result of careful research to solve the above-described problems, the present inventors succeeded in isolating from and purifying a protein (pectin lyase) from a filamentous fungus of the genus *Aspergillus*, which possesses characteristics a)-g) given below and possesses potent maceration activity under highly acidic conditions in the vicinity of pH 3.0, thereby achieving the present invention. This is the present invention according to claim 1.

a) Produced by a filamentous fungus belonging to the genus *Aspergillus*
b) Possesses maceration activity and pectin lyase activity
c) Molecular weight is 39,500
d) Optimal pH of maceration activity is 3.5
e) Optimal pH of pectin lyase activity is 4.5
f) Deactivates with boiling treatment for 15 minutes at 121° C., and
g) Has the N-terminus formed from the amino acid sequence given in SEQ ID NO: 1.

The protein according to claim 1 is described in a)-b) above and has a maceration activity derived from a filamentous fungus belonging to the genus *Aspergillus*. Among the filamentous fungi belonging to the genus *Aspergillus*, the species *Aspergillus niger* advantageously produces this protein.

In addition, the protein according to claim 1 possesses the characteristics described in c)-g) above, such that the molecular weight is 39,500, the optimal pH of maceration activity is 3.5, the optimal pH of pectin lyase activity is 4.5, it deactivates with boiling treatment for 15 minutes at 121° C., and its N-terminus is formed from the amino acid sequence given in SEQ ID NO: 1.

The present inventors succeeded in isolating and purifying a pectin lyase possessing maceration activity, using *Aspergillus niger* NBRC31125 as the productive strain. The N-terminal amino acid sequence (SEQ ID NO: 1) of this pectin lyase is identical to the sequence of the N-terminal side (amino acids 1-8 of SEQ ID NO: 2) of the amino acid sequence (SEQ ID NO: 2) coded by a pectin lyase gene described below (SEQ ID NO: 3 and SEQ ID NO: 4).

Therefore, the protein of the present invention includes a protein having the amino acid sequence given in SEQ ID NO: 2, as well as a protein having an amino acid sequence in which 1 or a plurality of amino acids in the amino acid sequence given in SEQ ID NO: 2 is (are) deleted, substituted, or added, and also possesses maceration activity. It should be noted that there is no particular limitation on the number of amino acids which are substituted in the present invention when "amino acids in the amino acid sequence given in SEQ ID NO: 2 is (are) deleted, substituted, or added," but if the number is 1-10 or on the order of 1-4, or if amino acids with similar characteristics are substituted, it becomes possible to increase the number which are substituted. Means for preparing proteins according to such amino acid sequences are well known to persons skilled in the art. This is the invention according to claim 2.

The pectin lyase produced in accordance with the present invention has outstanding pectolytic properties, and is suited for processing and enhancing the utility of plant tissues or plant tissue-derived substances containing pectin. The invention of the present invention according to claim 3 provides such an enzyme preparation. That is to say, the enzyme preparation of the present invention is an enzyme preparation containing the above protein, and is used for enhancing the processing and utility of plant tissues or plant tissue-derived substances by degrading pectin.

The present invention according to claim 4 is an enzyme preparation comprising the above enzyme preparation with the addition of any one or more components of cellulase, xylanase, protease, galactanase, arabinanase, mannanase, rhamnogalacturonase, pectin methylesterase, pectate lyase, and other pectin lyases and polygalacturonases.

When the protein of the present invention is used in an enzyme composition, it can be used alone, or it can be used as an enzyme composition which combines of any one or more components of cellulase, xylanase, protease, galactanase, arabinanase, mannanase, rhamnogalacturonase, pectin methylesterase, pectate lyase, and other pectin lyases and polygalacturonases. Selection of which component(s) to use can be suitably determined depending on the desired function, but when the enzyme composition combines other enzymes, it becomes possible to further increase the potency of its effect as a pectinase.

The enzyme composition of the present invention can be used in processing plant tissues and plant tissue-derived substances for use. In this Specification, there are no particular limitations on the range of plant tissues or plant tissue-derived substances, so all plant tissues may be used. The present invention can, for example, be applied to food products such as vegetables and fruits, or to juices, purees, pastes, strained residues or extracts thereof.

The method for producing single cells of plant tissue of the present invention according to claim 5 is a method for producing single cells of plant tissue which uses the above enzyme preparation as the maceration enzyme, comprising causing the maceration enzyme to act on the plant tissue under acidic conditions of pH 3.0-3.5, and preventing the growth of harmful microorganisms by means of the antibacterial activity of a pectin lysate, without needing a sterilizing heat treatment.

EXAMPLES

The present invention is described in detail with Working Examples and a Preferred Embodiment below. It should be noted that the present invention is not limited to the Working Examples.

The present inventors believed that if they could obtain a biological species possessing the ability to produce a maceration enzyme which operates efficiently under highly acidic conditions in the vicinity of pH 3.0, it would greatly contribute to the efficient production of the enzyme. They also believed that if they could isolate and purify a maceration enzyme derived from such a biological species, then it would be possible to perform maceration of plant tissue, efficiently producing a pectin hydrolysate having antibacterial activity, under highly acidic conditions in the vicinity of pH 3.0, while preventing the growth of harmful microorganisms regardless of the length of the enzymatic reaction time. The present invention was achieved on the basis of these considerations, and utilizes *Aspergillus* filamentous fungi which were found to have a high capacity to produce pectin lyase and which also possess maceration activity.

[A] Obtaining a Maceration Producing Microorganism Used in Implementing the Present Invention and a Maceration Enzyme from the Microorganism The present invention employs a microorganism which is an *Aspergillus* filamentous fungus as a biological source for obtaining a maceration enzyme. As long as such a microorganism is a filamentous fungus belonging to the genus *Aspergillus*, any strain may be used in the present invention. However, as a result of careful research, the present inventors found that it is advantageous to use *Aspergillus niger*, and even more advantageous to use the NBRC31125 strain of *Aspergillus niger*.

*Aspergillus niger* can be readily procured from various transfer organizations. For example, the *Aspergillus niger* NBRC31125 strain can be obtained via transfer from the Genetic Resource Preservation Section of the National Institute of Technology and Evaluation (NITE) Biological Resource Center (NBRC). Such an *Aspergillus* filamentous fungus used in the present invention has a high capacity to produce pectin lyase possessing maceration activity.

[B] Isolation of the Protein of the Present Invention (Pectin Lyase)

In order to obtain the maceration enzyme of the present invention, the *Aspergillus* filamentous fungus described above should be cultured, and the protein having maceration activity should be isolated from the culture product. In this Specification, "culture product" refers to a medium containing cultured *Aspergillus* filamentous fungal cells. There are no particular limitations on the medium used in culturing, as long as it is a medium to which pectin has been added to a medium capable of supporting *Aspergillus* filamentous fungi. For example, a potato-dextrose solid medium to which pectin has been added, or a wheat bran medium to which pectin has been added may be used, but according to the findings of the present inventors, it is most advantageous to use a wheat bran medium to which pectin has been added.

The pectin lyase of the present invention can be obtained from *Aspergillus* filamentous fungi by using a method having the following Steps 1-4, for example.

First, an *Aspergillus* filamentous fungus is cultured in a medium (e.g., a wheat bran medium to which pectin has been added) for 40-48 hours at 25-35° C. and a pH ranging from 5.0 to 7.0 (Step 1). The culture product is centrifuged to separate the solids from the culture supernatant (Step 2). Then, the culture supernatant is subjected to ion-exchange or gel filtration chromatography, ammonium sulfate precipitation and/or precipitation with an organic solvent such as ethanol, to separate out the protein as a fraction (Step 3).

Step 3 is described in further detail as follows. A sterile supernatant obtained by filtering and sterilizing the culture supernatant which was separated in Step 2 was placed into a dialysis tube and dialyzed against an initial buffer overnight to form a crude enzyme solution, and this was loaded onto an anion-exchange column which had been thoroughly equilibrated with the initial buffer, and thoroughly washed with this buffer. Then, the ionic strength of the buffer was changed using NaCl, and the protein was fractionated step-wise.

Next, the presence of maceration activity of the separated protein fraction was detected, making it possible to selectively obtain an enzyme fraction containing a maceration enzyme (Step 4). Detection of the presence of a maceration enzyme in Step 4 can be carried out, for example, by confirming if a protein fraction possesses maceration activity, but in cases where a protein which has maceration activity also has pectin lyase activity, the presence of pectin lyase activity is determined first, and then it can be determined whether or not maceration activity is present in an enzyme fraction having pectin lyase activity.

Maceration activity can be measured, for example, by immersing a sweet potato disc in the enzyme solution, and measuring the time elapsed until the sweet potato disc uniformly decays in the enzyme solution as a result of insoluble pectin being degraded by enzymatic action. In the alternative, other publicly-known methods may be used.

An example of a method for measuring pectin lyase activity is to measure over time the absorbance of the maximum absorption wavelength at 235 nm by unsaturated polygalacturonid formed as a result the substrate being degraded by enzymatic action. In the alternative, other publicly-known methods may be used.

[C] Methods for Measuring Maceration Activity and Pectin Lyase Activity

Examples of a method for measuring maceration activity and a method for measuring pectin lyase activity used in the Working Examples are described below.

1. Maceration Activity

A column 6 mm in diameter is removed from the center of a sweet potato using a cork borer. After using a knife to cut sweet potato discs about 0.3 mm thick, the discs are immersed for 60 seconds in 70% ethanol and then rinsed with distilled water. Into a test tube are placed 300 µL of enzyme solution with pH adjusted to 3.5 using HCl, and 200 µL of 50 mM acetate buffer (pH 3.5), and after these are mixed, a constant temperature is set at 30° C., and 3 of the above sweet potato discs are placed therein, and a reaction is initiated. Every 15 minutes after the reaction starts, agitation is carried out for 10 seconds using a test tube mixer, and the degree of decay is visually observed. The strength of the maceration activity is expressed by the reciprocal of the time needed for 2 of the 3 sweet potato discs to almost uniformly decay (Reference literature: Toshihiko Suganuma, Tetsuro Fukumoto, Youko Ikemizu, Katsuyuki Nakama, Shigeo Fujimoto, and Tomonori Nagahama, *Bulletin of the Faculty of Agriculture, Kagoshima University*, 37, 89-98, Mar. 16, 1987).

2. Pectin Lyase Activity (1) Preparation of Enzymatic Reaction Solution

First, 50 µL of a solution of 2 wt. % of pectin (SIGMA/P9436, derived from citrus fruit) adjusted to pH 4.5 using NaOH or HCl, and 50 µL of enzyme solution were prepared. The 50 µL of wt. 2% pectin solution was mixed with 400 µL of 50 mM acetate buffer (pH 4.5) to prepare in advance a total of 450 µL, to which 50 µL of enzyme solution is to be added for a total of 500 µL as an enzymatic reaction solution to be used when measuring activity. In order to ensure uniform diffusion of the substrate in the reaction solution and to achieve stabilization, NaCl is added to obtain a final concentration of 0.1 M.

(2) Measurement of Enzyme Activity

The enzyme solution and the enzymatic reaction solution without the enzyme solution are each incubated for 10 minutes at 25° C., after which 50 µL of the enzyme solution is mixed with 450 µL of the enzymatic reaction solution without the enzyme solution. An enzymatic reaction is then initiated, and measurements of absorbance at 235 nm are taken continuously for 10 minutes at 25° C. using a spectrometer. The amount of resulting unsaturated polygalacturonid is computed using a molecular absorbance coefficient of 5200 ($M^{-1}cm^{-1}$) (Paloma Sanchez-Torres, Jeap Visser, and Jacques A. E. Benen, *Biochem. J.*, 370, 331-337, Feb. 15, 2003), and 1 unit (1 U) of pectin lyase activity was set at the amount of unsaturated polygalacturonid formed per 1 µmmol of unsaturated digalacturonid per minute.

Detection and measurement of maceration activity and pectin lyase activity for each protein fraction are performed in this manner in Step 4. The protein fraction containing pectin lyase having maceration activity obtained as described above may be further purified using a Q-Sepharose High-Performance Column or a MonoQ Column (GE Healthcare Life Sciences), for example. Such purification makes it possible to obtain a purer pectin lyase with maceration activity from the fraction.

[D] Tests for Characterizing the Pectin Lyase of the Present Invention

Measurement of molecular weight, analysis of the N-terminal amino acid sequence, kinetic analysis, tests to determine optimal pH and pH stability, tests to determine maximum temperature, tests of the effects of metallic ions, and tests to measure maceration activity were performed in order to characterize the pectin lyase of the present invention. Moreover, comparisons with other pectin lyases are conducted in conjunction with investigations of the relationship between pectin lyase activity and maceration activity, and in addition, tests are conducted on the antibacterial activity of pectin lysates. First, the methods of bacterial culturing, preparation of the crude enzyme solution, and isolation/purification of the pectin lyase used in obtaining the pectin lyase of Working Example 1 used in these tests are described below.

Working Example 1

(1) Bacterial Culturing

After adding to 100 g of wheat bran an equivalent amount of purified water and 2 g of pectin and uniformly mixing them, the pH was adjusted to 7.0 using NaOH, and the mixture was evenly spread onto a vat having a bottom 20 cm×30 cm, and this was sterilized in an autoclave for 15 minutes at 121° C., resulting in a wheat bran medium. This medium was inoculated with conidiospores of the strain *Aspergillus niger* NBRC31125 obtained by preculturing with a potato dextrose/agar medium (Nissui Pharmaceutical Co., Ltd.), at 270 cells per 1 $cm^2$ of surface area, and then incubated for 46 hours at 30° C.

(2) Preparation of the Crude Enzyme Solution

To the medium was added a three-fold volume of purified water (including 1% NaCl), and enzyme extraction was carried out. The extract was filtered through filter paper, and a centrifuged supernatant of the filtrate was collected. To this centrifuged supernatant was added ammonium sulfate so as to dissolve to 90% saturation. After allowing to stand overnight at 4° C., centrifugation was carried out and the resulting precipitate was recovered, and this was dissolved again in a small quantity of 20 mM phosphate buffer (pH 6.2), to produce a concentrate. This concentrate was dialyzed overnight against the same buffer, resulting in a crude enzyme solution. The total amount of protein in the crude enzyme solution was computed using the Bradford Method, and was determined to be 9.01 mg. Using the same method, the pectin lyase activity of the crude enzyme solution was found to be 0.889 U/mg.

(3) Isolation and Purification of Pectin Lyase

The resulting crude enzyme solution was loaded onto a DEAE-Sepharose fast flow column which had been thoroughly equilibrated with a 20 mM phosphate buffer (pH 6.2), and after washing the column with the same buffer, NaCl was added to bring this buffer to 0-1 M, and step-wise elution of the enzyme was performed. The amount of the eluting protein was determined by monitoring the absorbance at 280 nm for each fraction, and the enzyme activity was determined by measuring the pectin lyase activity. Protein possessing pectin lyase activity was eluted with a phosphate buffer containing the unbound fraction and 0.4 M NaCl.

Next, the protein fractions found to have pectin lyase activity were recovered and mixed, and after dialyzing over night against the same buffer, the resulting material was loaded onto a Q-Sepharose High Performance Column (GE Healthcare Life Sciences) which had been thoroughly equilibrated with the above buffer, and after thoroughly washing with this buffer, elution of the enzyme was carried out using gradient elution, so that the NaCl concentration in the buffer was 0.3-0.6 M. Among the protein fractions determined to have pectin lyase activity, those protein fractions determined to have maceration activity according to the above method were recovered, and after performing dialysis in the same manner as previously, elution of the enzyme was performed again using a Q-Sepharose High Performance Column under the same conditions. As a result, an isolated and purified pectin lyase possessing maceration activity was eluted using 0.43 M NaCl. Isolation and purification were completed by confirming that there was a single band in SDS-PAGE (using a 10% polyacrylamide gel). Using the above-described method, the pectin lyase activity of the purified pectin lyase having maceration activity was found to be 54.7 U/mg, which is 61 times that of the above-described crude enzyme solution.

Various properties of the pectin lyase of Working Example 1 which was isolated and purified as described above, were determined as follows.

(4) Measurement of Molecular Weight

The molecular weight of the purified pectin lyase possessing maceration activity was estimated at about 39,500, as a result of analysis with SDS-PAGE (using a 10% polyacrylamide gel) as described above. The molecular weight marker Daiichi II (Daiichi Pure Chemicals Co., Ltd.) was used, and the standard molecular weights shown by these markers were 200 kDa, 116 kDa, 66 kDa, 42 kDa, 30 kDa, and 17 kDa.

In this Specification, the term "molecular weight" can refer to a value measured according to a publicly-known method for measuring molecular weight known by persons skilled in the art, such as mass analysis, light scattering, SDS-PAGE, and the like, but preferably, values measured by SDS-PAGE are used. However, some degree of error in measurement is unavoidable in measuring molecular weight. Therefore, when a "protein with a molecular weight of 39,500" appears in this Specification, it includes proteins for which the measured value of molecular weight by SDS-PAGE is 39,000-40,000.

(5) Analysis of N-Terminal Amino Acid Sequence

After performing SDS-PAGE, the isolated and purified pectin lyase having maceration activity was transferred to a PVDF membrane. The region of the membrane containing the pectin lyase having maceration activity purified on the PVDF membrane was removed with a knife to serve as a sample, and analysis of the N-terminal amino acid sequence of the pectin lyase having maceration activity was performed using a Procise 494 HT Protein Sequencing System. As a result of analysis, there were determined to be 8 amino acids. The sequence of these amino acids is given in SEQ ID NO: 1 below.

(6) Kinetic Analysis

In order to determine the kM value of the isolated and purified pectin lyase having maceration activity (SIGMA/P9561, derived from citrus fruit, degree of esterification <90%), a McIlvaine buffer (0.1 M citric acid, 0.2 M phosphoric acid) adjusted to pH 4.8 was used in measuring the enzyme activity when the final concentration of pectin was changed. As a result, the Km value was found to be 5.4 mg/mL and the Vmax value was found to be 140 U/mg, as computed from a Lineweaver-Burk plot.

(7) Test to Determine the Optimal pH and pH Stability of the Pectin Lyase

In order to determine the optimal pH for pectin lyase activity of pectin lyase having maceration activity produced from the strain *Aspergillus niger* NBRC31125, the enzyme activity at various pH levels was measured using the above-described enzymatic reaction solution with modified pH (the enzymatic reaction solution described in [C] 2. (1) above).

It should be noted that a 20 mM phosphate buffer was used for the pH 6.0-7.5 enzymatic reaction solution, and a 50 mM Tris-HCl buffer was used for the pH 7.5-9.5 enzymatic reaction solution. In cases where a McIlvaine buffer was used in a pH range of 3-6, the pectin lyase activity was measured in the same manner. Moreover, in order to determine the pH stability, the pH of enzyme solutions containing purified enzymes was adjusted to 3.0, 4.0, 5.0, 6.0, 7.0, 8.0, 9.0 and 10.0, using either HCl or NaOH. After allowing these enzyme solutions to stand for 24 hours at 4° C., the pectin lyase activity was measured at 25° C. using a 50 mM acetate buffer (pH 4.5).

The pH stability was evaluated using the formula (activity after standing/activity before standing)×100. As a result, the specific activity and the pH stability of pectin lyase at various pH levels are represented in the graph in FIG. 1, where 1.0 is pectin lyase at pH 4.5. The optimal pH for pectin lyase activity according to the present invention was 4.5 in the acetate buffer, and 4.8 in the McIlvaine buffer, and was thus found to be stable in a pH range of 3-6.

Figure 2:
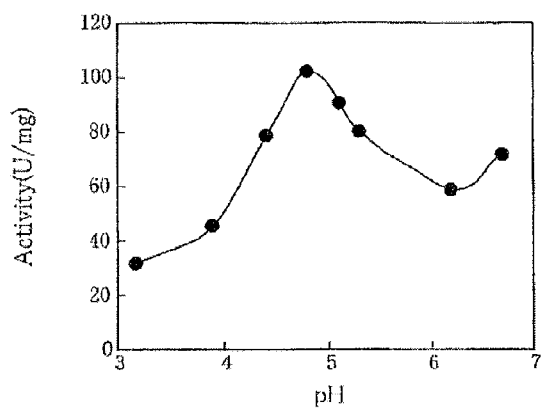
FIG. 2 is a graph showing experimental results confirming the pectin lyase activity of the enzyme preparation of the present invention.

In addition, under conditions of 30° C., and within a pH range of 3.0-7.0, a McIlvaine buffer was used to measure the pectin lyase activity when the ionic strength of the various buffers was adjusted to 0.5 using KCl. As a result, the optimal pH was 4.8 and the pectin lyase activity was 102 U/mg, as shown in FIG. 2.

(8) Test to Determine the Maximum Temperature of Pectin Lyase

Figure 3:
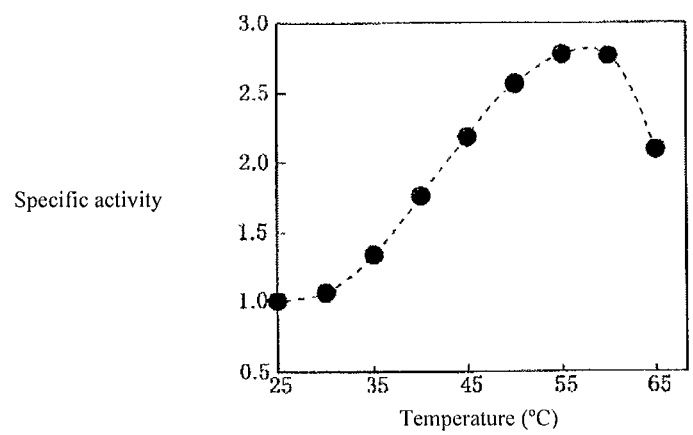
FIG. 3 is a graph showing experimental results confirming temperature ranges in which the pectin lyase of the present invention is active, showing the specific activity in terms of an activity of 1.0 at 25° C.

In order to determine the temperature range for pectin lyase having maceration activity produced from the strain *Aspergillus niger* NBRC31125, the pectin lyase activity was measured at various temperatures in a range of 25° C.-65° C. using the enzymatic reaction solution described in [C] 2. (1) above. Activity at various temperatures is shown in FIG. 3, where 1.0 is activity at 25° C. This enzyme was completely deactivated with boiling treatment for 15 minutes at 121° C.

(9) Tests of the Effects of Metallic Ions

Tests were conducted on the effects of metallic ions ($Ca^{2+}$, $Ba^{2+}$, $Co^{2+}$, $Cu^{2+}$, $Mg^{2+}$, $Mn^{2+}$, $Zn^{2+}$, and $Fe^{2+}$) of pectin lyase having maceration activity produced from the strain *Aspergillus niger* NBRC31125 on pectin lyase activity.

The test method involved the use of chlorides of various metals, and adjusting their final concentration in the enzymatic reaction solution to 1 mM, and calculating the percentage of change in activity depending on the presence or absence of metallic ions. The enzymatic reaction solution used a 50 mM acetate buffer and a pH of 4.5, and measurements were taken at 10-minute intervals at 25° C. The results are given in TABLE 1 below. When $Ca^{2+}$ was added, the activity was 120%, but when $Ba^{2+}$, $Co^{2+}$, $Mg^{2+}$, $Mn^{2+}$, and $Zn^{2+}$ were added, they had almost no effect on activity. The addition of $Fe^{2+}$ and $Cu^{2+}$ had a significant inhibitory effect on activity.

TABLE 1

| | Type of added metallic ion | | | | | | | |
|---|---|---|---|---|---|---|---|---|
| | $Ca^{2+}$ | $Ba^{2+}$ | $Co^{2+}$ | $Cu^{2+}$ | $Mg^{2+}$ | $Mn^{2+}$ | $Zn^{2+}$ | $Fe^{2+}$ |
| Activity (%) vs. non-addition of ions | 120 | 103 | 100 | 0 | 103 | 103 | 97 | 0 |

Following is a description of the maceration activity of pectin lyase having maceration activity produced from the strain *Aspergillus niger* NBRC31125.

(10) Tests to Measure Maceration Activity

A column 6 mm in diameter was removed from the center of a sweet potato (about 500 g) using a cork borer. After using a knife to cut sweet potato discs about 0.3 mm thick, the discs were immersed for 60 seconds in 70% ethanol and then rinsed with distilled water. Into a test tube were placed 300 μL of purified enzyme solution (1.30 μg/mL) and 200 μL of a buffer, and after these were mixed, a constant temperature was set at 30° C., and 3 of the above sweet potato discs were placed therein, and a reaction was initiated.

The buffers were 50 mM acetate buffers with pH 3.0, 3.5, 4.0, 4.5, 5.0, and 6.0, a 50 mM HEPES buffer with pH 7.0, and 50 mM Tris-HCl buffers with pH 8.0 and 9.0. After starting the reaction, stirring was carried out for 10 seconds with a test tube mixer every 15 minutes, and the degree of decay was visually observed. The strength of the maceration activity was expressed by the reciprocal of the time needed for 2 of the 3 sweet potato discs to almost uniformly decay.

Figure 4:
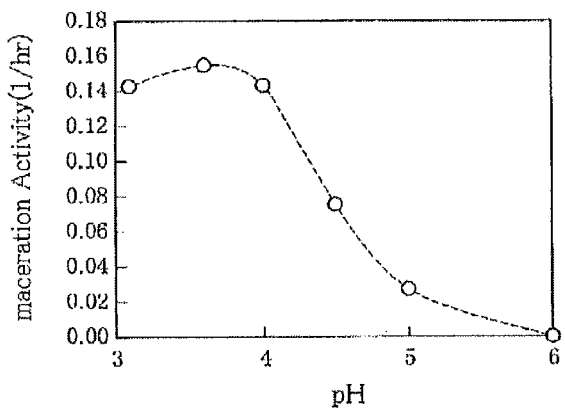
FIG. 4 is a graph showing experimental results confirming the relationship between pH and the potency of maceration activity of the pectin lyase of the present invention.

The results are as shown in the graph in FIG. 4. Although no decay occurred at all at pH 6.0, 7.0, 8.0, and 9.0, maceration activity was observed at pH 5.0 or lower, and the optimal pH for the above-described maceration activity was in the vicinity of 3.5. The maceration activity per 390 ng of purified pectin lyase having maceration activity was 0.15 (1/hr).

Figure 5:
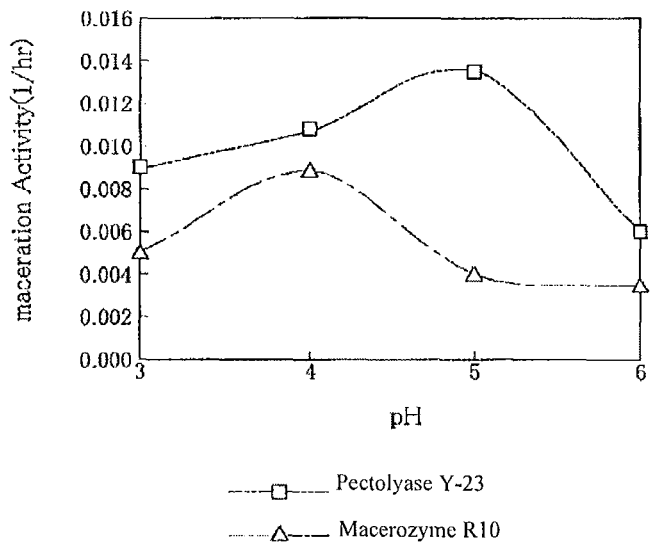
FIG. 5 is a graph showing the results of measurement of maceration activity of the enzyme preparation of a commercial enzyme preparation, in order to evaluate the potency of maceration activity of the pectin lyase of the present invention.

In order to evaluate the strength of the maceration activity of the pectin lyase of the present invention, in a Comparative Example, two commercially available enzyme preparations, Macerozyme R10 and Pectolyase Y-23 were dissolved in purified water so that the amount of protein in the respective enzyme solutions was 1.30 μg/ml, and these were subjected to the test described above. The results are summarized in FIG. 5.

The optimal pH and the maceration activity per 390 ng of protein were pH 4.0 and 0.0088 (1/hr) for Macerozyme R10, and pH 5.0 and 0.0134 (1/hr) for Pectolyase Y-23. The specific activity of the purified pectin lyase of the present invention having maceration activity at pH 3.0 was 27.7 times that of Macerozyme R10, and 15.6 times that of Pectolyase Y-23. It was found that under acidic conditions of pH 3.0, the maceration activity of the pectin lyase of the present invention is able to macerate plant tissues at efficiency very much greater than the existing commercially available enzyme preparations.

(11) Relationship Between Pectin Lyase Activity and Maceration Activity, and Comparison with Other Pectin Lyases In order to study the relationship between the maceration activity and the pectin lyase activity of the pectin lyase of the present invention, the pectin lyase activity and the maceration activity were measured within a pH range of 3.0 and 7.0.

As a comparative control, a pectin lyase A (PLA=PLII) produced by the strain *Aspergillus niger* N400 (=CBS120.49=NRRL3=JCM12729) was used in measuring the pectin lyase activity and the maceration activity in the manner described above. PLA was obtained by applying the method given in [D] (1) and (2) above to the strain *Aspergillus niger* N400, to prepare a crude enzyme solution by incubating for 48 hours at 30° C. in a minimal medium containing pectin, and then following the method given in (3), purification of pectin lyase was carried out until a single band was formed in SDS-PAGE (using a 10% polyacrylamide gel) (Reference literature: J. A. M. Harmsen, M. A. Kusters-van Someren, and J. Visser, *Curr. Genet.*, 18, 161-166, August 1990). It should be noted that the fact that the purified pectin lyase was PLA was confirmed by the SDS-PAGE estimated molecular weight of 38.5 kDa, and by the fact that the pH dependency and specific activity were in almost complete agreement with those of the N400 strain PLA, as reported in a study by Paloma Sanchez-Tones et al. (Paloma Sanchez-Tones, Jaap Visser, and Jacques A. E. Benen, *Biochem. J.*, 370, 331-337, Feb. 15, 2003). In addition, PLA is reported to be the principal enzyme contained in Ultrazyme (Novo) known as a commercial pectinase preparation possessing elevated activity (Margo A. Kusters-Van Someren, Jan A. M. Harmsen, Harry C. M. Kester, and Jaap Visser, *Curr. Genet.*, 20, 293-299, September 1991). However, to date, no studies have been published pertaining to the maceration activity of PLA.

The pectin lyase activity was measured as described below. First, a McIlvaine buffer was used in the enzymatic reaction solution, and an HM pectin substrate (SIGMA/P9561, derived from citrus fruit, degree of esterification <90%) was used to obtain a final concentration of 3 mg/mL. The ionic strength of the enzymatic reaction solution was adjusted in advance to I=0.3 or 0.5, using KCl, and the enzyme solution was 50 μL, and the total amount of the enzymatic reaction solution was 500 μL. Measurements were carried out in the same manner as in [C] 2. (2) (Paloma Sanchez-Tones, Jaap Visser, and Jacques A. E. Benen, *Biochem. J.*, 370, 331-337, Feb. 15, 2003), except that the temperature was 30° C.

Figure 8:
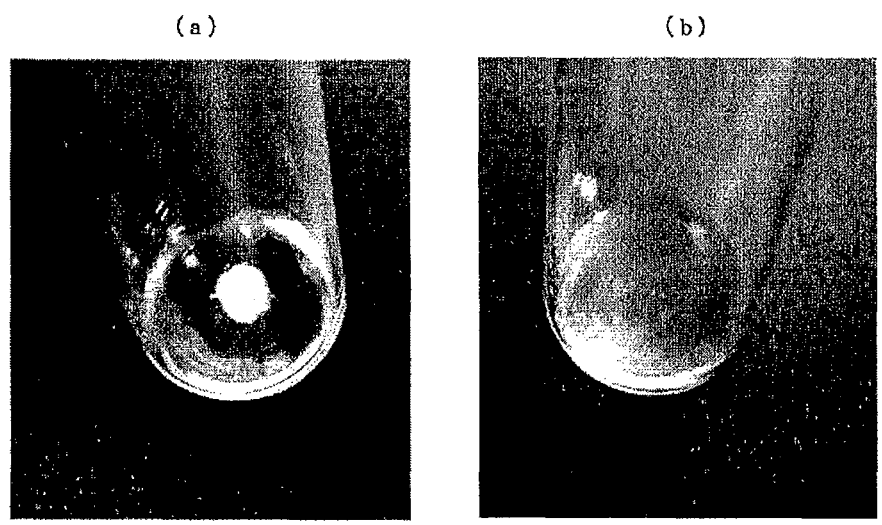
FIG. 8 (a) is a photograph showing an example of a state in which a sweet potato disc in a test solution exhibits no decay at all immediately after the start of a reaction, and (b) is a drawing photograph showing an example in which a sweet potato disc in a test solution exhibits almost uniform decay.

The maceration activity was measured as described below. First, sweet potato discs were prepared in the same manner as described above. Then, 50 μL of enzyme solution and 450 μL of buffer were placed in a test tube and mixed, forming a test solution held at a constant temperature of 45° C., then 1 of the above sweet potato discs were placed therein, and a reaction was initiated. A McIlvaine buffer was used as the buffer, and the ionic strength of the test solution (total of 500 μL) was adjusted in advance to I=0.3 or 0.5, using KCl. After the reaction started, stirring was carried out in the manner described above, and the degree of decay was visually observed. Three specimens each were prepared under the various conditions, and reactions of specimens under identical conditions were initiated simultaneously. The strength of the maceration activity under those conditions was expressed by the reciprocal of the time needed for any 2 of the sweet potato discs of the 3 specimens under identical conditions (total of 3) to almost uniformly decay. It should be noted that FIG. 8 (*a*) shows an example of a state in which a sweet potato disc in a test solution exhibits no decay at all immediately after the start of the reaction, and FIG. 8 (*b*) is a photograph showing an example in which a sweet potato disc in a test solution exhibits almost uniform decay.

As a result of the measurements, the pectin lyase activity and maceration activity of the pectin lyase of the present invention were in agreement with an optimal pH of 4.0 when I=0.3, and they were in agreement with an optimal pH of 5.0 when I=0.5. When a McIlvaine buffer was used, HM pectin degradation with I=0.5, and for maceration with I=0.3 were suited for both the pectin lyase of the present invention and the N400 strain PLA.

The specific maceration activity was 7400 (1/(hr·mg) per 1 mg of this pectin lyase, and 2542 (1/(hr·mg) per 1 mg of N400 strain PLA, so this pectin lyase had about 3 times the activity of N400 strain PLA. On the other hand, the specific pectin lyase activity was 102 (U/mg) per 1 mg of this pectin lyase, and 110 (U/mg) per 1 mg of N400 strain PLA, which were about equal. The ratio of the maceration activity to the pectin lyase activity (=maceration activity/pectin lyase activity) of 1 mg of the two enzymes was respectively 72.5 for the pectin lyase of the present invention and 23.1 for the N400 strain PLA, thereby confirming that the pectin lyase of the present invention possesses a much more potent maceration activity than was predicted on the basis of the strength of the pectin lyase activity.

Figure 6:
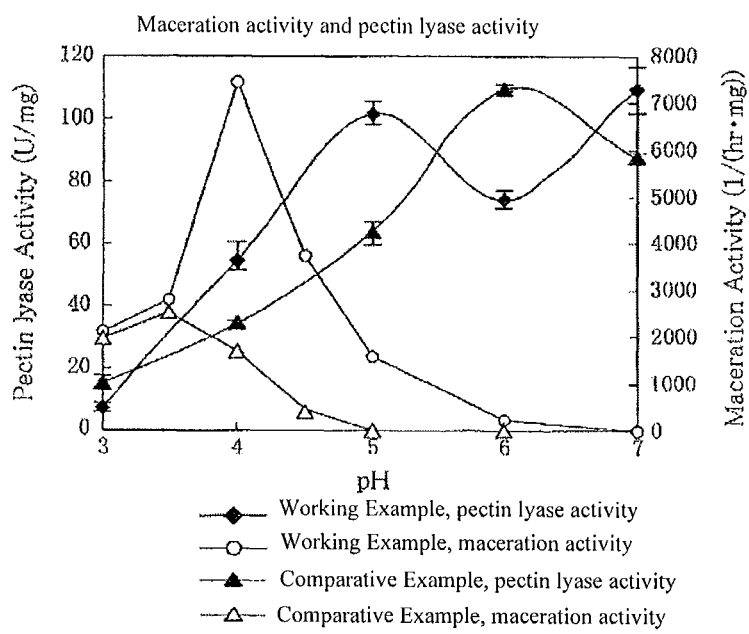
FIG. 6 is a graph showing maceration activity and pectin lyase activity of the pectin lyase of the present invention.

FIG. 6 is a graph showing the results of measurements of specific pectin lyase activity (I=0.5) and specific maceration activity (I=0.3) per 1 mg of protein for the pectin lyase of this Working Example and for the N400 strain PLA of the Comparative Example, respectively. The darkened diamond shape represents pectin lyase activity (mean±standard deviation, N=5) of the pectin lyase of this Working Example, the white circle represents maceration activity of the pectin lyase of this Working Example, the darkened triangle represents pectin lyase activity (mean±standard deviation, N=5) of the Comparative Example (N400 strain PLA), and the white triangle represents maceration activity of the Comparative Example (N400 strain PLA).

These results show that the pectin lyase of the present invention has about 3 times more potent maceration activity than the *Aspergillus niger* N400 strain PLA. Pectin lyase having this maceration activity is a PLA mutant with 9 amino acids which differ from the N400 strain PLA, as described below. It is particularly advantageous in maceration of plant tissues, because its specific maceration activity per 1 mg of protein is about 3 times more potent than the N400 strain PLA.

(12) Antibacterial Tests of Pectin Lysates

An enzymatic reaction was carried out to produce a pectin lysate from pectin, using the pectin lyase of the present invention, which possesses maceration activity. The antibacterial activity of the resulting pectin lysate was then evaluated (Reference literature: Koki Yokotsuka, Toshihide Matsudo, Tadae Kushida, Shigeo Inamine, and Tomoyoshi Nakajima in *Hakkogaku Kaishi*, 62, 1-7, Jan. 25, 1984).

(i) Preparation of the Pectin Lysate

To 8.5 mL of 50 mM acetate buffer was added 1 mL of 3% pectin aqueous solution (SIGMA/P9436, degree of methoxylation <68%) dissolved in sterilized water, and finally 0.5 mL of enzyme solution (500 ng purified pectin lyase of the present invention having maceration activity:maceration activity at pH 3.0=0.18 (hr$^{-1}$) was added, to form an enzymatic reaction solution.

0.5 mL of a 2% Macerozyme A (Registered trademark of Yakult Pharmaceutical Co.) solution (maceration activity=0.18 (hr$^{-1}$) at pH 3.0) and 0.5 mL of a 0.16% Pectolyase Y-23 solution (maceration activity=0.18 (hr$^{-1}$) at pH 3.0) were used as enzyme solutions of Comparative Examples. These enzyme solutions both had maceration activity 0.18 (hr$^{-1}$) at pH 3.0, and the final concentration in the test solutions of commercial enzyme preparations were 0.1% for Macerozyme A and 0.008% for Pectolyase Y-23, which are concentrations typically used in the maceration of plants. The commercial enzyme solutions were formed by dissolving the respective enzyme powders in sterilized water, then filtering with a sterilized disposable membrane filter (Whatman Co., pore size 0.45 µm), and then using filtrates. It should be noted that the maceration activity of each filtrate was identical to that prior to filtration.

The enzymatic reaction solutions were allowed to stand for 6 hours at 30° C., and after heating for 10 minutes in a bath to deactivate the enzymes, the respective reaction solutions were ultrafiltered with a 0.45 µm filter, and the filtrate was freeze dried and pulverized to produce pectin lysates. It should be noted that three acetate buffers were used, with pH 3.0, 4.0, and 5.0, and pectin lysates were prepared by reacting at each pH. In addition, a control was prepared by adding 0.5 mL of sterilized water instead of the enzyme solutions, but otherwise, the freeze-dried powders were produced in entirely the same manner.

(ii) Preparation of Antibacterial Test Solution

Using *Bacillus subtilis* ATCC 6633 as the indicator bacterium for measuring antibacterial activity, a bacterial culture (28,000 CFU/mL) was produced with a shaking culture for 24 hours at 30° C. Next, liquid media were produced which had the following final concentrations: dried yeast extract (Nacalai Tesque) 2.5 g/L, peptone (Wako Pure Chemical Industries, Ltd.) 5.0 g/L, D-(+)-glucose (Nacalai Tesque) 1.0 g/L. Using a 50 mM acetate buffer, these liquid media were adjusted to pH 3.0, 4.0, and 5.0, and then heated at 121° C. for 15 minutes. After heating, there were no changes in the pH of the media.

The total amount of the above pectin lysates or undegraded pectin produced by reacting at the same pH as the liquid media were dissolved in 9.0 mL of the above liquid media, after which 1 mL (2,800 CFU/mL) of 1/10 diluted the above bacterial culture was added, resulting in the antibacterial test solutions.

(iii) Tests

Figure 7:
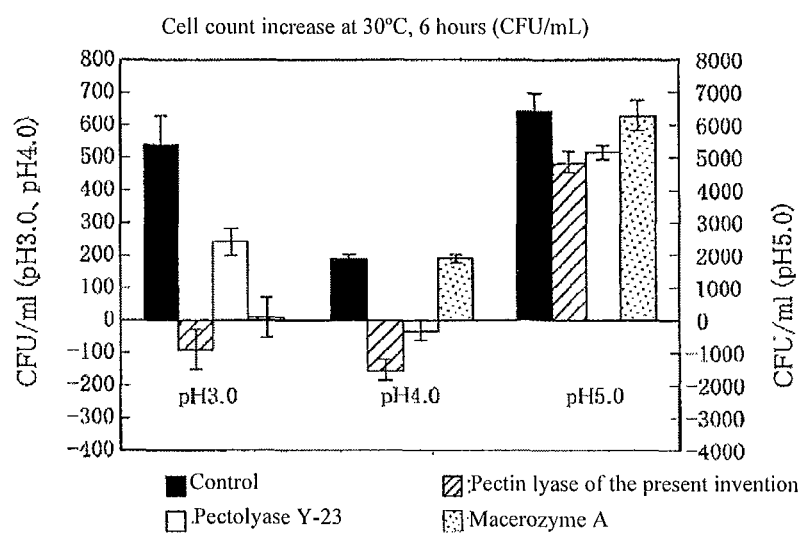
FIG. 7 is a graph showing experimental results confirming the antibacterial activity and bactericidal activity of pectin lysates formed by the pectin lyase of the present invention.

The culture was performed at 30° C. as a stationary culture. Using an agar medium (standard agar culture for measuring total viable cell count, Nissui Pharmaceutical Co., Ltd.) at pH 7.0, the total viable cell count was measured for each test solution immediately after incubation and 6 hours after incubation. Using the pour plate method, the cell count was measured after inoculating with the test solution or a dilution thereof for 48 hours at 35° C. When measurements were made using this method, no differences were found in the total cell count or in the colony surface area, either in the test solution inoculated with the bacterial culture (1/10 dilution, 1 mL) or in the test solution immediately after starting the test. The bacteria used in the above tests were determined to be in the logarithmic growth phase by making cell count measurements of the pH 5.0 control after 6 hours, 12 hours, and 24 hours (doubling time about 80 minutes). FIG. 7 is a graph showing the increase in cell count [=(viable cell count in each test solution)–(viable cell count of inoculate)] of the enzyme solutions and the control test solutions. The graph shows the mean±standard deviation for 5 specimens under the various conditions.

TABLE 2 below shows the growth inhibition rate [=(increase in viable cell count)/(increase in viable cell count of control with corresponding pH)–(viable cell count of inoculate)×100] for the above enzyme solutions. The growth inhibition rate is 100% when the increase in viable cell count is negative, which indicates bactericidal activity. In TABLE 2, the figures in parentheses indicate the bactericidal rate [={(viable cell count of inoculate)–(viable cell count of test solution)}/(viable cell count of inoculate)×100] for test solutions which were determined to exhibit bactericidal activity.

TABLE 2

| pH | 3.0 | 4.0 | 5.0 |
|---|---|---|---|
| Working Examples | 100% (33%) | 100% (55%) | 23% |
| Comparative Example 1 (Pectolyase Y-23) | 56% | 100% (12%) | 20% |
| Comparative Example 2 (Macerozyme A) | 100% | 0% | 2% |

As a result of these tests, bactericidal activity was determined in the pectin lysate produced by the pectin lyase of the present invention under conditions of pH 3.0 and 4.0, exhibiting a potency, unreported until now, which was determined to be 4 times higher than exhibited under the condition of pH 4.0 by the pectin lysates produced by Pectolyase Y-23. Due to the bactericidal activity and antibacterial activity of the pectin lysate, it became possible to more efficiently inhibit the growth of harmful bacteria and partially sterilize or completely sterilize than by using pectin lysates produced by other existing enzymes.

When the pectin lyase of the present invention is used, it is possible to implement an enzymatic reaction with microbial growth being inhibited, even if the pH of the reaction solution fluctuates during the enzymatic reaction, as long as the pH is kept within a range of 3.0-4.0. It is also possible to partially sterilize or completely sterilize the reaction solution by utilizing the bactericidal effect of the pectin lysate. It should be noted that when the pectin lyase of the present invention is used to produce a pectin lysate, pectin extracted from a plant may be used as a substrate on which this pectin lyase acts, or the plant itself may be used containing the pectin in the intercellular layers.

As described above, one embodiment of the present invention is a protein produced by *Aspergillus niger* NBRC31125, possessing maceration activity and pectin lyase activity, with a molecular weight of 39,500, and with the N-terminus formed from the amino acid sequence given in SEQ ID NO: 1. In addition, this protein exhibits maceration activity at an optimal pH of 3.5 and pectin lyase activity at an optimal pH of 4.5, and was determined to deactivate when subjected to boiling treatment for 15 minutes at 121° C., and possesses distinctive pectin lyase activity in a pH range of 3-6.

Moreover, when the ionic strength of the enzymatic reaction solution was adjusted to I=0.3, the optimal pH of 4.0 was in agreement for both the pectin lyase activity and the maceration activity of the protein of the present invention, and it was found that the specific maceration activity per 1 mg of protein at the optimal pH was 3 times more potent than that of the known pectin lyase *Aspergillus niger* N400 PLA. It was also found that pectin lysates formed by the protein of the present invention have potent antibacterial and bactericidal activity in the pH range 3.0-4.0.

It should be noted that in this Specification, where it states that a protein "possesses maceration activity," it means that the protein acts on insoluble pectin in plant tissue, and possess activity which isolates single cells from the plant tissue. In this Specification, "possesses pectin lyase activity" means that the protein cleaves the $\alpha$-1,4 bond of polygalacturonic acid with a $\beta$-elimination reaction, and possess activity which forms C4-C5 unsaturated bonds at the unreduced termini. Such activity can be measured using the method set forth in [C] above, but other publicly-known methods may also be used.

[E] Gene Coding for the Protein According to Present Invention

Following is a description of the gene coding for the protein according to the present invention. The pectin lyase gene of the present invention is a gene which codes for a pectin lyase possessing the maceration activity described in this Specification. There are no particular limitations on the type of gene, which may be naturally derived DNA, recombinant DNA, or chemically synthesized DNA, and it may be a cDNA clone or a genomic DNA clone. "A gene which codes for a pectin lyase possessing the maceration activity described in this Specification" means a gene fragment which is able to produce a pectin lyase possessing the maceration activity described in this Specification when it is expressed. There are no particular limitations on the gene, but in detail, it may be a DNA fragment which includes cDNA which codes for a pectin lyase possessing the above-described maceration activity described in this Specification, or it may be a genomic DNA fragment which codes for a pectin lyase of the present invention which possesses maceration activity, and which includes an intron in the coding region. It should be noted that in this Specification, "gene consisting of DNA" and "gene formed from DNA" mean the same thing as "gene formed from DNA."

The present inventors succeeded in obtaining a gene which codes for a pectin lyase of the present invention which codes for maceration properties. That is to say, the present inventors used the method described above to obtain and purify a pectin lyase produced by *Aspergillus niger* NBRC31125 which has maceration activity, and specified the N-terminal amino acid sequence thereof (SEQ ID NO: 1).

Next, using the RT-RCR method, the present inventors produced cDNA using as a template the total RNA obtained from *Aspergillus niger* NBRC31125, and then performed PCR using a degenerate primer estimated from the above N-terminal amino acid sequence (SEQ ID NO: 1) using the cDNA as a template, thereby obtaining a partially amplified fragment of a pectin lyase gene which possesses the desired maceration activity. Then, the base sequence of this partially amplified fragment was determined by an ordinary method. The resulting base sequence is shown in SEQ ID NO: 4.

The present inventors also succeeded in using a partially amplified fragment to clone a partial gene (from a portion coding for the N-terminus to the stop codon) in genomic DNA which codes for a pectin lyase mature protein which possesses the desired maceration activity. SEQ ID NO: 3 shows the base sequence of the gene for pectin lyase which possesses maceration activity in the DNA genome.

Such DNA formed from the base sequence shown in SEQ ID NO: 3 is a gene coding for pectin lyase which possesses the desired maceration activity shown in SEQ ID NO: 2. The DNA formed from the base sequence shown in SEQ ID NO: 3 includes 4 introns (bases 288-341, 468-513, 611-668, and 903-953 in SEQ ID NO: 3). Therefore, when the DNA formed from the base sequence given in SEQ ID NO: 3 is expressed in a eukaryotic cell, preferably a filamentous fungus, and more preferably a cell of an *Aspergillus* filamentous fungus, the mRNA transcribed from DNA forms mature mRNA with above intron removed by splicing, and this mRNA is translated, making it possible to produce a pectin lyase which possesses maceration activity from the amino acid sequence given in SEQ ID NO: 2.

It thus becomes possible to produce the pectin lyase of the present invention which possesses maceration activity, by using DNA formed from the base sequence shown in SEQ ID NO: 3. It is also possible to obtain the DNA formed from the base sequence shown in SEQ ID NO: 3 by amplifying the target DNA fragment with PCR, using a sense primer and an antisense primer suitably designed and prepared on the basis of the base sequence given in SEQ ID NO: 3, with genomic DNA extracted from *Aspergillus niger* NBRC31125 as a template. The design and preparation of the primer, as well as setting of the reaction conditions for PCR have been already optimized by those skilled in the art. The gene according to the present invention includes genes composed of DNA formed from the base sequences given in SEQ ID NO: 3.

The pectin lyase formed from the amino acid sequence shown in SEQ ID NO: 2 is also coded by the cDNA having the base sequence shown in SEQ ID NO: 4. Therefore, when the DNA formed from the base sequence shown in SEQ ID NO: 4 is expressed in a prokaryotic cell and/or a eukaryotic cell, the mRNA transcribed from the DNA is translated, thereby making it possibly for a pectin lyase possessing maceration activity to be produced from the amino acid sequence shown in SEQ ID NO: 2. Accordingly, the gene consisting of DNA formed from the base sequence shown in SEQ ID NO: 4 is also included in the gene according to the present invention. The DNA formed from the base sequence shown in SEQ ID NO: 4 can be obtained by amplifying the target DNA fragment by performing PCR using as a template cDNA produced from total RNA extracted from *Aspergillus niger* NBRC31125, using a sense primer and an antisense primer designed and prepared on the basis of the 5' side sequence and the 3' side sequence of the base sequence.

However, the pectin lyase gene of the present invention is not limited to one formed as above from DNA consisting of the base sequences given in SEQ ID NOS: 3 and 4. More generally, the pectin lyase gene having maceration activity according to the present invention is one which codes for the protein possessing maceration activity according to the present invention. Thus, the gene of the present invention also includes a gene coding for a protein formed from the amino acid sequence given in SEQ ID NO: 2, and a gene coding for a protein which has an amino acid sequence in which 1 or a plurality of amino acids in the amino acid sequence given in SEQ ID NO: 2 is (are) deleted, substituted, or added, and also which possesses maceration activity.

The pectin lyase gene of the present invention is also a DNA which codes for a protein hybridized under stringent conditions from DNA formed entirely from the base sequence given in SEQ ID NO: 4 or from DNA formed partly from a complementary base sequence, and which also possesses a maceration activity. In the present invention, "stringent conditions" refer to conditions under which a specific hybrid is formed, and conditions under which a non-specific hybrid is not formed.

These conditions are, for example, conditions under which DNAs having highly homologous nucleic acids, in other words, DNAs with homology of 90% or greater, and preferably 95% or greater, which code for a protein possessing maceration activity hybridize with each other, and conditions under which nucleic acids with a lower degree of homology do not hybridize with each other. In further detail, an example of stringent hybridization conditions include a sodium salt concentration of 15-750 mM, preferably 50-750 mM, and more preferably 300-750 mM; a temperature of 25-70° C., preferably 50-70° C., and more preferably 55-65° C.; and a formamide concentration of 0-50%, preferably 20-50%, and more preferably 35-45%. Furthermore, even in cases where the hybridization washing conditions are sodium salt concentration of 15-600 mM, preferably 50-600 mM, and more preferably 300-600 mM and a temperature of 50-70° C., preferably 55-70° C., and more preferably 60-65° C., these can be included in "stringent conditions" according to the present invention.

The pectin lyase gene of the present invention as described above can be obtained by means of a nucleic acid amplification reaction such as PCR, using as a template cDNA which is chemically synthesized or cloned, or a cDNA library or a genomic DNA library, or by means of hybridizing a cDNA library or genomic DNA library, using as a probe the DNA fragment having the given base sequence. There are no limitations on the organism from which the cDNA library or the genomic DNA library may be derived, but an *Aspergillus* filamentous fungus is preferable, and an organism belonging to *Aspergillus niger* is particularly advantageous, and the strain *Aspergillus niger* NBRC31125 is most advantageous.

Furthermore, the pectin lyase gene of the present invention can be prepared by modifying the base sequence of a pectin lyase gene isolated from a natural source, by using a mutation method such as site-directed mutagenesis. The mutation method may employ a publicly-known technique such as Kunkel mutagenesis, the Gapped duplex method, or the like, or a technique based thereon. For example, mutation may be performed using a mutation kit which employs site-directed mutagenesis [e.g., the Mutan(R)-K, Mutan(R)-Express Km, or Mutan (R)-Super Express Km Series, or the LA PCRTM in vitro Mutagenesis Series Kit, all products of Takara Bio Inc.]. It should be noted that the sequence of the resulting pectin lyase gene of the present invention should be confirmed by sequencing. Base sequencing may be performed using a publicly-known method (e.g., using an automated base sequencer such as a DNA Sequencer manufactured by ABI Co.). It is also possible to prepare a mutant gene coding for a protein possessing maceration activity by modifying the gene of the present invention by introducing a mutation by site-directed mutagenesis. Even if the gene of the present invention is modified using such a mutation method, the resulting mutation is included within the scope of the gene of the present invention, and is therefore included in the gene of the present invention.

[F] Preparation of a Recombination Vector

In accordance with the present invention, a recombination vector is provided which contains the pectin lyase gene of the present invention. For convenience in handling, the gene of the present invention is preferably cloned in a vector, using a recombination vector. This recombination vector can be easily prepared by using an ordinary method for linking the pectin lyase gene of the present invention to a recombination vector which is available in this industry (e.g., plasmid DNA, phage DNA, or the like).

Specific examples of plasmid DNA which can be advantageously used as a vector include *Escherichia coli*-derived plasmids such as pBR322, pUC18, pUC19, pBluescript, and the like; *Staphylococcus aureus*-derived plasmids such as pUB110, pTP5, and the like; and yeast-derived plasmids such as YEp13, YCp50, and the like. Specific examples of phage DNA include, but are not limited to M13mp18/19 and λ phage (e.g., Charon4A, Charon21A, EMBL3, EMBL4, λgt10, λgt11, and λZAP) and the like. In some cases, a *Staphylococcus aureus* shuttle vector (e.g., pHY300PLK and the like), a yeast shuttle vector (e.g., pAUR101DNA, pAUR112DNA and the like, or a filamentous fungus shuttle vector (e.g., pAUR316DNA and the like), may be used advantageously. Moreover, an animal virus such as a retrovirus or a vaccinia virus vector, or an insect virus vector such as baculovirus may be also used.

An example of a method for inserting the pectin lyase gene of the present invention into a vector is described in Sambrook, J. et al., *Molecular Cloning: A Laboratory Manual*, Second Edition, Cold Spring Harbor Laboratory, 1.53 (1989). For the sake of simplicity, a commercial ligation kit (e.g., a Takara Bio Co. product) may be used.

An expression vector is particularly useful for the purpose of producing the pectin lyase of the present invention. There are no particular limitations on the type of expression vector, as long as it expresses the pectin lyase gene of the present invention in various types of prokaryotic and/or eukaryotic host cells, and as long as it functions to produce the pectin lyase of the present invention. Advantageous examples include a pET vector (e.g., Novagen) as an *Escherichia coli*-derived expression vector, pYES2 (Invitrogen) as a yeast-derived expression vector, and pBacPAK8/9 (Clontech) as an insect-derived expression vector, among others.

In general, expression vectors require a variety of elements such as a transcription promoter, a terminator, a rhibozomal binding site, and the like, for expression in a host organism, as well as selection markers indicating that a vector is held within a cell, cis elements such as polylinkers, enhancers, and the like, splicing signals, polyA signals, rhibozomal binding sequences (SD sequences), secretion factor sequences, and other useful sequences can be linked as needed in order to simply insert a gene in the proper direction in a vector.

A vector containing a secretion factor sequence suited for the host cell is useful when producing a recombinant protein by preparing a transfectant using a recombination expression vector. This secretion factor sequence may be specifically excised from protein coded by the recombinant gene in the vector, using a predetermined protease, after being secreted to the culture supernatant. Examples of selection markers include a difolate reductase gene, an ampicillin resistance gene, a neomycin resistance gene, and the like.

The pectin lyase gene of the present invention is linked in a position and direction suitable for expression in a vector such as described above.

Moreover, the gene of the present invention may be directly introduced into a host cell genome by homologous recombination. In such cases, a suitable targeting vector is produced with the recombined gene of the present invention. Examples of vectors which can be used for this purpose include publicly known gene-targeting vectors such as Cre-loxP and the like.

[G] Preparation of a Transfectant and Production of Pectin Lyase Using the Transfectant A tranfectant (transfection cell) can be prepared by introducing the pectin lyase gene of the present invention into a host cell by a publicly-known method familiar to persons skilled in the art. Then, pectin lyase can be produced by culturing this transfectant to produce pectin lyase in a culture product and isolating it.

There are no particular limitations on the host cell, as long as it is compatible with the expression vector of the present invention and can undergo transfection. A variety of cells may be used, including natural cells and artificial recombinant cells normally used in the technical field of the present invention. Examples include bacteria such as *Escherichia coli* and *Staphylococcus aureus*, yeast cells, insect cells, animal cells (e.g., mammalian cells), plant cells, and the like. It is particularly advantageous to use *Escherichia coli*, yeast cells, or plant cells in the present invention. In further detail, it is advantageous to use *Escherichia coli* or yeast cells in the production of the pectin lyase of the present invention. Furthermore, pectin hydrolysates (oligogalacturonic acid) are known to induce a resistance response in plants, and it is advantageous to use cells of plants such as soybeans or rice, in order to increase the resistance of plants when the pectin lyase gene of the present invention is introduced.

Transfection can be accomplished by employing a typical method, such as calcium phosphate transfection or calcium chloride/rubidium chloride transfection, electroporation, lipofection, particle gun transfection, PEG transfection, and the like. Selection of the transfectant can be performed using an established method, and a selection marker introduced into a recombination vector is typically used.

The method for culturing the transfectant is a typical method used in culturing a host organism. For example, there are no particular limitations on the medium used for culturing a transfectant obtained by using a microorganism such as *Escherichia coli* or yeast cells as the host, as long as it is a medium which efficiently cultures the transfectant, and includes a carbon source, a nitrogen source, and inorganic salts which the host can assimilate. As needed, antibiotics such as ampicillin, tetracycline, and the like may be added to the medium.

Moreover, in cases in which a transfected microorganism is cultured using an expression vector containing an inductive promoter, an inducer can be added to the medium as needed. For example, if a transfected microorganism is cultured using an expression vector which includes a GAL1 promoter site, galactose or the like may be added to the medium.

There are no particular limitations on the culturing conditions for the transfectant used in the present invention, but they should be suitable for a host organism used in transfection. When pectin lyase accumulates in the cell after culturing, the cell can be crushed and the pectin lyase is collected. If the pectin lyase is secreted to outside of the cell, it can be directly collected from the culture product, and it can be collected as a culture supernatant by removing the cells from the culture product by centrifugation or the like. In the present invention, it is also possible to produce the pectin lyase using a cell-free protein expression system, instead of transfection.

"Cell-free protein expression system" refers to an in vitro transcription-translation system or an in vitro translation system in a test tube or the like, involving a reagent such as amino acids required for translation which is added to a suspension produced by mechanically disrupt the cell structure of a host organism. An example of an advantageous cell-free protein expression system is a commercially available kit such as EasyXpress Protein Synthesis Kit (QIAGEN).

The resulting pectin lyase can be used as a dialyzed crude enzyme solution after concentrating the above-mentioned culture supernatant with ultrafiltration or the like, and performing ammonium sulfate fractionation. The resulting pectin lyase may also be used after isolating it from the above-mentioned culture product (from the disrupted cell solution, culture liquid, or supernatant thereof) or from the above-mentioned crude enzyme solution and purifying it, using ammonium sulfate salting out and/or ethanol organic vehicle precipitation, gel filtration chromatography, ion-exchange chromatography, affinity chromatography, or the like, either separately or in combination.

Common molecular biology techniques (DNA electrophoresis, methods for recovering electrophoresis DNA from gel, restriction enzyme digestion, PCR, base sequencing, and the like) used in the steps of the present invention such as those described above, are explained, for example, in Sambrook, J. et al., *Molecular Cloning: A Laboratory Manual*, Second Edition, Cold Spring Harbor Laboratory, 1989, and are publicly-known methods which are familiar to persons skilled in the art.

[H] Method of Obtaining the Pectin Lyase Gene of the Present Invention

Following is a more detailed description of the method for obtaining the pectin lyase gene of the present invention.

Working Example 2

(1) Extraction of Total RNA

A minimal medium ($NaNO_3$ 6 g/L, KCl 0.52 g/L, $MgSO_4 \cdot 7H_2O$ 0.52 g/L, $KH_2PO4$ 1.52 g/L, $FeCl_3$ 0.4 mg/L, and ZnCl$_2$ 0.4 mg/L, with substrate pH adjusted to 6.5 with NaOH; Reference literature: Pontecorvo, G. *Advances in Genet.*, 5, 141-238, 1954) containing 1% pectin was inoculated with conidiospores of *Aspergillus niger* NBRC31125, and then shaking cultured for 48 hours at 30° C., after which the mycelia were harvested by filtering the culture liquid with a miracloth filter. These mycelia were then frozen at −20° C., pulverized under liquid nitrogen in an emulsion mortar and pestle, after which 19.8 µg of total RNA was extracted using an illustra RNAspin kit (GE Healthcare Life Sciences).

(2) Synthesis of Single-Strand Complementary DNA (cDNA)

To a template of 1.0 µg of extracted total RNA was added 50 µmol of oligo (dT)$_{20}$ primer, and predetermined amounts of reverse transcription reaction buffer, 10 mMdNPT mix, and 0.1 MDTT, and finally, 200 U of a reverse transcriptase (SuperScript III, Invitrogen) was added, and reverse transcription reactions were carried out for 15 minutes at 50° C., 60° C., and 70° C., resulting in 20 µL of cDNA at 176 ng/µL, produced by the reverse transcription reactions of mRNA.

(3) Cloning of cDNA

A PCR reaction was carried out on template of the resulting cDNA, using a degenerate primer 5'-GTIGGIGTIWSNG-GNWSNGC-3' (SEQ ID NO: 5) designed on the basis of 8 N-terminal amino acid sequences sequenced according to [D] (5) above as a sense primer, and oligo (dT)$_{20}$ as an antisense primer. Here, I is inosine, W is A or T, S is G or C, N is A or C or G or T. It should be noted that the PCR reaction solution contains 50 pmol of sense primer, 50 pmol of antisense primer, as well as predetermined amounts of 2.5 mMdNTP mix, 10×PCR reaction buffer [500 mM KCL, 100 mM Tris-HCl (pH 8.3)], 25 mM MgCl$_2$, and sterile distilled water, to which 176 ng of cDNA and 2.5 U of heat-resistant polymerase (Takara Taq, Takara Bio Inc.) were added, for a total amount of 50 µL. The PCR reaction was carried out using a thermal cycler Program Temp Control System PC320 (Astec), with 40 reaction cycles at 94° C.:30 sec, 50° C.:30 sec, and 72° C.:90 sec.

When the reaction product was sampled and applied to ordinary agarose gel electrophoresis (1.3% agarose) (see Sambrook et al., *A Laboratory Manual*, Second Edition, Cold Spring Harbor Press, Cold Spring Harbor, N.Y., 1989), a DNA fragment was detected as a single band having a size of about 1100 bp (base pairs). This DNA fragment was extracted and purified from the gel using an ordinary method (see Sambrook et al. above), resulting in a template for base sequencing.

When this template was sequenced using an Applied Biosystems 3730×1 analyzer (Applied Biosystems), a base sequence of about 1050 bp was determined. Since the resulting base sequence contained a base sequence 5'-TCCG-GCTCTGC-3' (SEQ ID NO: 6) which can be present in the degenerate primer designed above, a PCR reaction under the above conditions was carried out on the above cDNA template, using as a sense primer a degenerate primer 5'-GTNG-GNGTNTCCGGCTCTGC-3' (SEQ ID NO: 7) which was redesigned on the basis of the N-terminal amino acid sequence (SEQ ID NO: 1) and the information in the base sequence of SEQ ID NO: 6, and using as a antisense primer oligo (dT)$_{20}$. Following that, the resulting reaction product was similarly applied to agarose gel electrophoresis, and as a result, a DNA fragment was detected as a single band having a size of about 1100 bp. This DNA fragment was likewise extracted from the gel and purified, resulting in a template for base sequencing. When this template was sequenced in the same manner as previously, the base sequence of 1077 bp shown in SEQ ID NO: 4 was obtained. This base sequence a base sequence (bases 1-24 of Base sequence 4) which is able to code for the N-terminal amino acid sequence of pectin lyase having the desired maceration activity as determined above. It was therefore concluded that a partial clone of the pectin lyase gene having the desired maceration activity was produced. In addition, the base sequence given in SEQ ID NO: 4 includes the stop codon (bases 1078-1080 of SEQ ID NO: 4).

(4) DNA Extraction

A minimal medium (see Pontecorvo, G. above) containing 1% glucose was inoculated with conidiospores of *Aspergillus niger* NBRC31125, and then shaking cultured for 48 hours at 30° C., after which the mycelia were harvested by filtering the culture liquid with sterilized gauze. These mycelia were then suspended in 1 mL of 10 mM Tris-HCl, to which glass beads were added, and vigorous stirring was carried out using a beater. After that, the insoluble matter was centrifuged at 6,000 G for 10 minutes, resulting in 0.5 mL of a DNA solution. To this solution was added 1 mL of phenolchloroform (1:1), and these were mildly mixed for 15 minutes, and then centrifuged at 10,000 G for 10 minutes.

The upper layer aqueous fraction was recovered and 1 mL of phenolchloroform (1:1) was added again, and these were mildly mixed for 15 minutes, and then centrifuged at 10,000 G for 10 minutes. The upper layer aqueous fraction was recovered, 50 µL of 3 M sodium acetate and 1 mL of 99.5% cold ethanol were added, and these were mixed. After allowing to stand for 1 hour at a temperature of −20° C., the mixture was centrifuged at 10,000 G for 10 minutes. The DNA precipitate was lightly rinsed with 70% ethanol, and then airdried. After that, 50 µL of TE buffer was added to dissolve the DNA precipitate, resulting in 161 µg/mL of a DNA extract.

(5) Cloning of Genomic DNA

Next, a sense primer 5'-GTCGGCGTGTCCGGCTCTGC-3' (SEQ ID NO: 8) and an antisense primer 5'-TTACAGGT-TGCCCTGACCGG-3' (SEQ ID NO: 9) were designed and prepared on the basis of the information in the base sequence of SEQ ID NO: 4 for the cDNA obtained as described above, and a PCR reaction was carried out, using as a template the genomic DNA obtained as described above. It should be noted that the PCR reaction solution included the sense primer 20 pmol, the antisense primer 20 pmol, and predetermined amounts of 2.5 mM dNTP mix, 10×PCR reaction buffer [500 mM KCl, 100 mM Tris-HCl (pH 8.3)], 25 mM MgCl2, and sterilized water, to which were added DNA 80 ng, and heat-resistant polymerase (Takara Ex Taq, Takara Bio Inc.) 2.5 U, for a total amount of 50 µL, with 40 reaction cycles at 94° C.:30 sec, 55° C.:30 sec, and 72° C.:90 sec. The resulting PCR solution was applied to agarose gel electrophoresis, and as a result, a DNA fragment was clearly detected as a single band having a size of about 1300 bp, and his DNA fragment was likewise extracted from the gel and purified, resulting in a DNA fragment for base sequencing and analysis. Accordingly, sequencing resulted in SEQ ID NO: 3 which includes a sequence coding for the N-terminal amino acids of the genomic DNA.

(6) Amino Acid Sequencing and Gene Sequencing of the Pectin Lyase of the Present Invention When the base sequence of SEQ ID NO: 3 of the resulting genomic DNA was compared with the base sequence of SEQ ID NO: 4 of the cDNA, there were determined to be 4 likely introns (bases 288-341, 468-513, 611-668, and 903-953 in SEQ ID NO: 3). The base sequence in SEQ ID NO: 3 of the genomic DNA includes a stop codon (bases 1287-1289 in SEQ ID NO: 3), and base sequence obtained by removing the above introns from this base sequence matches SEQ ID NO: 4. It was therefore concluded that the base sequence resulting from the removal of the stop codon (bases 1078-1080 in SEQ ID NO: 4) from the base sequence given in SEQ ID NO: 4 is a base sequence coding from the N-terminus to the C-terminus of this pectin lyase.

The entire amino acid sequence of the mature protein of the pectin lyase possessing this maceration activity was determined from the base sequence of SEQ ID NO: 4 and from the 359 amino acids shown in SEQ ID NO: 2. When a homology search (BLAST) using a database (swissprot) was conducted on this amino acid sequence, it was determined that the pectin lyase having this maceration activity is a PLA mutant possessing 9 amino acids which differ from the known pectin lyase A which is *Aspergillus niger* N400 PLA.

[I] Preparation of Powder from Single Cells and Measurement of Total Viable Cell Count Following is a description of preparation of powder from single cells of a plant, using pectin lyase possessing maceration activity obtained from *Aspergillus niger* NBRC31125 and measurement of the total viable cell count.

Working Example 3

(1) Bacterial Culturing 20 plates of a minimal agar medium (see Pontecorvo, G. above) containing 1% pectin and 1.5% agar adjusted to pH 5.0 using NaOH was inoculated with conidiospores of *Aspergillus niger* NBRC31125 obtained by preculturing with a potato dextrose/agar medium (Nissui Pharmaceutical Co., Ltd.), at 270 cells per 1 $cm^2$ of surface area, and then incubated for 46 hours at 30° C.

(2) Preparation of Crude Enzyme Solution

After cutting the medium, a 3-fold volume of purified water (containing 1% NaCl) was added to the medium, and enzyme extraction was carried out at 4° C. for 3 hours. The extracted solution was filtered using filter paper, the filtrate was centrifuged, and the supernatant was collected. Then, 900 mL of the centrifuged supernatant was dissolved with ammonium sulfate to 90% saturation, and then allowed to stand overnight at 4° C. After that, the precipitate resulting from centrifugation was recovered, and this was re-dissolved in a small quantity of purified water, resulting in a concentrate. This concentrate was dialyzed overnight against purified water to obtain 22.5 mL of a crude enzyme solution. The total amount of protein in the crude enzyme solution was computed using the Bradford Method, and was determined to be 1.26 mg.

(3) Preparation of Powder from Single Cells and Measurement of Total Viable Cell Count 100 g of 5 mm squares of cut broccoli (cores) was prepared, and ethanol was used to disinfect only the surface thereof. To 10 mL of the above crude enzyme solution was added 40 mL of sterilized water for a total of 50 mL, and then 30 g of the above broccoli was immersed in enzymatic reaction solution A [corresponding to a maceration activity of 4.3 $(hr^{-1})$] of the Working Examples with the pH adjusted to 3.0 using citric acid (food additive: Konishi Toshikazu Shoten), and an enzymatic reaction was carried out for 24 hours at 30° C.

As a comparative control, Macerozyme A (Registered trademark of Yakult Pharmaceutical Co.) was added to 50 ml of sterilized water to obtain 0.5% concentration, and enzymatic reaction solution B [corresponding to a maceration activity of 4.7 $(hr^{-1})$] of Comparative Example 1 likewise with pH adjusted to 3.0 using citric acid, and further, Macerozyme A (Registered trademark of Yakult Pharmaceutical Co.) was added to 50 ml of sterilized water to obtain 0.5% concentration, and in addition, enzymatic reaction solution C [corresponding to a maceration activity of 3.3 $(hr^{-1})$] of Comparative Example 2 with pH adjusted to 6.0, were prepared and applied to the same testing as above. It should be noted that all of the glassware used had been sterilized, and all operations, such as unsealing of the packaging of powdered reagents and the enzymatic reactions, were conducted in clean benches.

After the enzymatic reactions were completed, residues were removed from the enzymatic reaction products by filtration using a mesh, the filtrates were centrifuged for 10 minutes at 1,500 G, the supernatants were removed, the precipitates containing single-cell formations were recovered, and these were each uniformly suspended in 20 mL of sterilized water, after which they were freeze-dried and pulverized. The yields (%) from the fresh single cell raw material powders and viable cell counts are shown in TABLE 3 below. The enzyme preparation of the present invention has a viable cell count of 1,000 cells/g, which satisfies the standards (3,000 cells/g or lower) for powdered beverages. It should be noted that in measuring the viable cell count, a pH 7.0 standard agar medium for measuring viable cell count (Nissui Pharmaceutical Co., Ltd.) was used.

TABLE 3

| Enzyme used | pH at start of enzymatic reaction | Yield (%) | Viable cell count (cells/g) |
|---|---|---|---|
| Enzyme solution A (Working Example) | 3.0 | 3.6 | $1 \times 10^3$ or lower |
| Enzyme solution B (Comparative Example 1) | 3.0 | 3.6 | $7 \times 10^3$ |
| Enzyme solution C (Comparative Example 2) | 6.0 | 3.4 | $2 \times 10^5$ |

Therefore, the enzyme preparation according to the present invention possesses potent maceration activity sufficient to be effective even under highly acidic conditions in the vicinity of pH 3.0, and the pectin lysates with high a high degree of methylesterification which were formed exhibited potent antibacterial activity. It was thus confirmed that even under mild enzymatic reaction conditions at normal temperatures, the antibacterial activity of the pectin lysates effectively inhibited the growth of harmful bacteria. In addition, the method for producing single cells of plant tissue according to the present invention employs the enzyme preparation of the present invention as a maceration enzyme. When the method of the present invention is used to produce single cells of plant tissue, the growth of harmful bacteria is inhibited by the antibacterial activity of the pectin lysates, making sterilizing heat treatment unnecessary. Thus, the maceration activity is effective under acidic conditions of pH 3.0-3.5.

The present invention is not limited to the above examples, and the preferred embodiment may, of course, be advantageously modified within the scope of the technical ideas recited in the claims.

The invention claimed is:

1. An isolated protein having the characteristics a)-g) below:
   (a) Endogenously produced by *Aspergillus niger* strain NBRC31125;
   (b) Possesses maceration activity and pectin lyase activity;
   (c) Molecular weight of 39,000-40,000 as measured by SDS-PAGE;
   (d) Specific maceration activity of 7400/(hr·mg) at pH 4.0;
   (e) Optimal pH of 4.5 for pectin lyase activity;
   (f) Deactivates with boiling treatment for 15 minutes at 121° C.; and
   (g) Has an N-terminus consisting of the amino acid sequence of SEQ ID NO: 1.

2. An isolated protein comprising the amino acid sequence of SEQ ID NO: 2.

3. An enzyme preparation comprising the isolated protein according to claim 1, wherein the enzyme preparation is used for processing plant tissues or plant tissue-derived substances by degrading pectin.

4. The enzyme preparation of claim 3 further comprising any one or more components of cellulase, xylanase, protease, galactanase, arabinanase, mannanase, rhamnogalacturonase, pectin methylesterase, pectate lyase, and other pectin lyases and polygalacturonases.

5. A method for producing single cells of plant tissue using an enzyme preparation of claim 3 as a maceration enzyme, comprising contacting the enzyme preparation of claim 3 with the plant tissue under acidic conditions of pH 3.0-3.5.

6. A recombinant vector comprising an isolated polynucleotide encoding a protein comprising the amino acid sequence of SEQ ID NO:2.

7. A recombinant vector comprising an isolated polynucleotide comprising the nucleotide sequence of SEQ ID NO:4.

8. A recombinant vector comprising an isolated polynucleotide comprising the nucleotide sequence of SEQ ID NO:3.

9. The isolated protein of claim 1, wherein the protein consists of the amino acid sequence of SEQ ID NO: 2.

* * * * *

UNITED STATES PATENT AND TRADEMARK OFFICE
CERTIFICATE OF CORRECTION

PATENT NO. : 8,691,536 B2  Page 1 of 1
APPLICATION NO. : 13/502869
DATED : April 8, 2014
INVENTOR(S) : Nakano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 35 days.

Signed and Sealed this
Twenty-ninth Day of September, 2015

Michelle K. Lee
*Director of the United States Patent and Trademark Office*